US006235533B1

(12) United States Patent
Tsipursky et al.

(10) Patent No.: US 6,235,533 B1
(45) Date of Patent: May 22, 2001

(54) METHOD OF DETERMINING THE COMPOSITION OF CLAY DEPOSIT

(75) Inventors: Semeon J. Tsipursky, Lincolnwood; Don D. Eisenhour, Grayslake; Gary W. Beall, McHenry, all of IL (US); Mark Clarey, Tupelo; James Edwards, Aberdeen, both of MS (US)

(73) Assignee: AMCOL International Corporation, Arlington Heights, IL (US)

( * ) Notice: Subject to any disclaimer, the term of this patent is extended or adjusted under 35 U.S.C. 154(b) by 0 days.

(21) Appl. No.: 09/040,633

(22) Filed: Mar. 18, 1998

(51) Int. Cl.[7] .......................... G01N 33/00; G01N 33/24; G01N 33/38; C04B 33/00
(52) U.S. Cl. .............................. 436/72; 501/141
(58) Field of Search ................ 436/72; 501/141

(56) References Cited

U.S. PATENT DOCUMENTS

| 2,035,546 | 3/1936 | Hamilton | 167/24 |
|---|---|---|---|
| 3,419,460 | 12/1968 | Ure | 161/162 |

(List continued on next page.)

FOREIGN PATENT DOCUMENTS

| 1 642 122 | 7/1970 | (DE) . |
|---|---|---|
| 0 205 281 A3 | 12/1986 | (EP) . |
| 0 335 653 A1 | 10/1989 | (EP) . |
| 0 358 415 A1 | 3/1990 | (EP) . |
| 0 479 031 A1 | 4/1992 | (EP) . |
| 0 645 181 A2 | 3/1995 | (EP) . |
| 0 761 739 A1 | 3/1997 | (EP) . |
| 1 146 668 | 3/1969 | (GB) . |
| 1 565 362 | 4/1980 | (GB) . |
| WO 93/04117 | 3/1993 | (WO) . |
| WO 93/04118 | 3/1993 | (WO) . |
| 0 548 940 A1 | 6/1993 | (WO) . |
| WO 93/11190 | 6/1993 | (WO) . |

OTHER PUBLICATIONS

C. W. Francis, "Adsorption of Polyvinylpyrrolidone on Reference Clay Minerals", Soil Science, vol. 115, No. 1, 1973, pp. 40–54.
A. Usuki, et al., "Synthesis of nylon 6–clay hybrid", J. Mater. Res., vol. 8, No. 5, May 1993, pp. 1179–1184.

(List continued on next page.)

*Primary Examiner*—Arlen Soderquist
*Assistant Examiner*—Latoya J. Cross
(74) *Attorney, Agent, or Firm*—Marshall, O'Toole, Gerstein, Murray & Borun

(57) ABSTRACT

A method of determining a quantity of amorphous $SiO_2$-containing impurities in a montmorillonite clay sample comprising the steps of:

(a) analyzing the clay sample to determine the weight percent of $SiO_2$ contained in the clay sample;

(b) analyzing the clay sample for non-montmorillonite $SiO_2$-containing crystalline components;

(c) calculating the weight percent of $SiO_2$ from step (a) that is derived from the montmorillonite and amorphous $SiO_2$-containing impurities by lowering the weight percent of $SiO_2$ in step (a) based on the non-montmorillonite $SiO_2$-containing crystalline impurities found in step (b); and (d) determining the amorphous $SiO_2$-containing impurity portion of the $SiO_2$ calculated in step (c) by further lowering the amount of $SiO_2$ from step (c) until the amount of montmorillonite-derived $SiO_2$ is consistent with one or more properties of the clay sample, the amount of further lowering being proportional to an amount of amorphous $SiO_2$-containing impurities contained in the clay sample.

30 Claims, 15 Drawing Sheets

U.S. PATENT DOCUMENTS

| | | | |
|---|---|---|---|
| 3,419,517 | 12/1968 | Hedrick et al. | 260/37 |
| 3,515,626 | 6/1970 | Duffield | 161/162 |
| 3,773,708 | 11/1973 | Takahashi et al. | 260/41 R |
| 3,795,650 | 3/1974 | Burns | 260/33.4 R |
| 3,912,532 | 10/1975 | Simone | 106/308 N |
| 3,929,678 | 12/1975 | Laughlin et al. | 252/526 |
| 4,125,411 | 11/1978 | Lyons | 106/291 |
| 4,210,572 | 7/1980 | Herman et al. | 260/40.4 |
| 4,251,576 | 2/1981 | Osborn et al. | 428/331 |
| 4,400,485 | 8/1983 | Mukamal et al. | 524/444 |
| 4,431,755 | 2/1984 | Weber et al. | 523/203 |
| 4,434,075 | 2/1984 | Mardis et al. | 252/315.2 |
| 4,472,538 | 9/1984 | Kamigaito et al. | 523/202 |
| 4,500,670 | 2/1985 | McKinley et al. | 524/445 |
| 4,546,145 | 10/1985 | Kishida et al. | 524/780 |
| 4,600,744 | 7/1986 | Libor et al. | 524/446 |
| 4,613,542 | 9/1986 | Alexander | 428/290 |
| 4,624,982 | 11/1986 | Alexander | 524/446 |
| 4,739,007 | 4/1988 | Okada et al. | 524/789 |
| 4,789,403 | 12/1988 | Rice | 106/417 |
| 4,798,766 | 1/1989 | Rice | 428/404 |
| 4,810,734 | 3/1989 | Kawasumi et al. | 523/216 |
| 4,842,651 | 6/1989 | Ravet et al. | 106/487 |
| 4,849,006 | 7/1989 | Knudson, Jr. | 71/64.11 |
| 4,875,762 | 10/1989 | Kato et al. | 350/357 |
| 4,889,885 | 12/1989 | Usuki et al. | 524/443 |
| 4,894,411 | 1/1990 | Okada et al. | 524/710 |
| 4,920,171 | 4/1990 | Hutton, Jr. et al. | 524/446 |
| 5,032,546 | 7/1991 | Giannelis et al. | 501/3 |
| 5,032,547 | 7/1991 | Giannelis et al. | 501/3 |
| 5,091,462 | 2/1992 | Fukui et al. | 524/504 |
| 5,102,948 | 4/1992 | Deguchi et al. | 524/789 |
| 5,164,440 | 11/1992 | Deguchi et al. | 524/444 |
| 5,164,460 | 11/1992 | Yano et al. | 624/445 |
| 5,204,078 | 4/1993 | Tateyama et al. | 423/331 |
| 5,206,284 | 4/1993 | Fukui et al. | 524/504 |
| 5,229,451 | 7/1993 | Carter et al. | 524/493 |
| 5,248,720 | 9/1993 | Deguchi et al. | 524/444 |
| 5,326,500 | 7/1994 | Friedman et al. | 252/378 |
| 5,340,558 | 8/1994 | Friedman et al. | 423/328.1 |
| 5,385,776 | 1/1995 | Maxfield et al. | 428/297 |
| 5,391,437 | 2/1995 | Miyasaka et al. | 528/425.5 |
| 5,414,042 | 5/1995 | Yasue et al. | 524/789 |
| 5,428,094 | 6/1995 | Tokoh et al. | 524/379 |
| 5,506,046 | 4/1996 | Andersen et al. | 524/446 |
| 5,508,072 | 4/1996 | Andersen et al. | 524/446 |
| 5,514,734 | 5/1996 | Maxfield et al. | 523/204 |
| 5,552,469 | 9/1996 | Beall et al. | 524/445 |
| 5,578,672 | 11/1996 | Beall et al. | 624/446 |
| 5,667,886 | 9/1997 | Gough et al. | 428/331 |
| 5,698,624 | 12/1997 | Beall et al. | 524/445 |
| 5,760,106 | 6/1998 | Pinnavaia et al. | 523/209 |
| 5,910,523 | 6/1999 | Hudson | 523/213 |
| 5,981,029 | 11/1999 | Harada et al. | 428/143 |
| 5,994,445 | 11/1999 | Kaschel et al. | 524/444 |
| 6,071,988 | 6/2000 | Barbee et al. | 523/210 |
| 6,084,019 | 7/2000 | Matayabas, Jr. et al. | 524/445 |

OTHER PUBLICATIONS

Y. Kojima, et al., "Mechanical Properties Of Nylon 6–Clay Hybrid", J. Mater. Res., vol. 8, No. 5, May 1993, pp. 1185–1189.

K. Suzuki, et al., "Preparation Of Delaminated Clay Having A Narrow Micropore Distribution In The Presence Of Hydroxyaluminum Cations and Polyvinyl Alcohol", Clays and Clay Minerals, vol. 36, No. 2, 1988, pp. 147–152.

R. Levy, et al., "Interlayer Adsorption of Polyvinylpyrrolidone On Montmorillonite", Journal of Colloid and Interface Science, vol. 50, No. 3, Mar. 1975, pp. 442–450.

D.J. Greenland, "Adsorption Of Polyvinyl Alcohols By Montmorillonite", Journal of Colloid Science, 18, (1963) pp. 647–664.

R.A. Vaia, et al., "Synthesis and Properties of Two–Dimensional Nanostructures by Direct Intercalation of Polymer Melts in Layered Silicates", Chem. Mater. 1993, 5, pp. 1694–1696.

R.A. Vaia, et al., "New Polymer Electrolyte Nanocomposites: Melt Intercalation of Poly(ethylene oxide) in Mica–Type Silicates", Advanced Materials 1995, 7, No. 2, pp. 154–156.

A. Akelah, et al., "Synthesis and Characterization of Epoxyphilic montmorillonites", Clay Minerals (1994) 29, pp. 169–178.

C.E. Clapp, et al., "Adsorption Studies Of A Dextran On Montmorillonite", Trans. 9th Int. Cong. Soil Sci., 1968, vol. 1, pp. 627–634.

H.G.G. Dekking, "Preparation And Properties Of Some Polymer–Clay Compounds", Clays and Clay Minerals, 1964, 12, pp. 603–616.

A. Usuki, et al., "Characterization and Properties of Nylon 6—Clay Hybrid", (source and date unknown), pp. 651–652.

G.W. Brindley, et al., "Preparation And Solvatio Properties Of Some Variable Charge Montmorillonites", Clays and Clay Minerals, 1971, vol. 18, pp. 399–404.

A. Okada, et al., "A Solid State NMR Study On Crystalline Forms Of Nylon 6", Journal of Applied Polymer Science, (1989), vol. 37, pp. 1363–1371.

A. Usuki, et al., Swelling Behavior Of Montmorillonite Cation Exchanged For ω–Amino Acids By ε–Caprolactam, J. Mater. Res., vol. 8, No. 5, May 1993, pp. 1174–1178.

Y. Kojima, et al., "One–Pot Synthesis Of Nylon 6–Clay Hybrid", Journal of Polymer Science: Part A: Polymer Chemistry, vol. 31, (1993), pp. 1755–1758.

Y. Kojima, et al., "Fine Structure Of Nylon–6–Clay Hybrid", Journal of Polymer Science: Part B: Polymer Physics, vol. 32 (1994), pp. 625–630.

B.K.G. Theng, "Clay–Polymer interactions: Sumary And Perspectives", Clays and Clay Minerals, vol. 30, No. 1 (1982) pp. 1–9.

Sugahara, et al., "Clay–Organic Nano–Composite; Preparation of a Kaolinite–Poly(vinylpyrrolidone) Intercalation Compound", *Journal of the Ceramic Society of Japan*, International Edition, vol. 100, No. 4, Apr. 1, 1992, pp. 420–423.

Ogawa, et al., "Preparation Of Montmorillonite–Polyacrylamide Intercalation Compounds And The Water Absorbing Property", Clay Science, vol. 7, 1989 Tokyo, Japan, pp. 243–251.

Wu, et al., "Structural, thermal, and electrical characterization of layered nanocomposites derived from sodium–montmorillonite and polyethers", Chemical Abstracts, vol. 119, No. 4, Jul. 26, 1993 Columbus, Ohio, US, Abstract No. 31017r.

Bujdak, et al., "The reaction of montmorillonite with octadecylamine in solid and melted state", Chemical Abstracts, vol. 118, No. 26, Abstract No. 257609b, p. 166 (Jun. 28, 1993), Columbus, Ohio (US).

Yano, et al., "Synthesis And Properties Of Polyimide–Clay Hybrid", Polymer Preprints, ACS, Apr. 1991, pp. 65–66.

Giannelis, et al., "Synthesis And Processing Of Ceramics: Scientific Issues", Materials Research Society Symposium Proceedings, vol. 249 (1992), pp. 547–558.

Sanchez Camazano, M. et al., "Factors influencing interactions of organophosphorus pesticides with montmorillonite", *Chemical Abstracts*, vol. 98, No. 19, May 9, 1983, Columbus, Ohio, US, Abstract No. 156367.

T. Lan, et al., "Clay–Epoxy Nanocomposites:Relationships Between Reinforcement Properties And The Extent Of Clay Layer Exfoliation", *Polym. Mater. Sc. Eng.*, 73, pp. 206–297 (1995).

Moore, et al. "X–Ray Diffraction and the Identification and Analysis of Clay Minerals", ©1989 by Oxford University Press, Inc., pp. 102–271.

FIG. 1

| Grid #1 | |
|---|---|
| Element | wt. % |
| O | A1 |
| Na | A2 |
| Mg | A3 |
| Al | A4 |
| Si | A5 |
| P | A6 |
| S | A7 |
| K | A8 |
| Ca | A9 |
| Ti | A10 |
| Cr | A11 |
| Mn | A12 |
| Fe | A13 |
| Total | A14 |

(Grid #1A)

| $Fe^{2+}/(Fe^{2+}+Fe^{3+})$ |
|---|
| B1 |

| (Grid #2) | | |
|---|---|---|
| Clay Composition | | # cat./ |
| Oxide | Wt. % | f.unit |
| SiO2 | K1 | L1 |
| TiO2 | K2 | L2 |
| Al2O3 | K3 | L3 |
| Fe2O3 | K4 | L4 |
| FeO | K5 | L5 |
| MnO | K6 | L6 |
| MgO | K7 | L7 |
| CaO | K8 | L8 |
| Na2O | K9 | L9 |
| K2O | K10 | L10 |
| | K11 | L11 |

| Set Admixtures (Grid #7) | | |
|---|---|---|
| Admix. | wt. % | Suggest |
| Opal-CT | C1 | |
| Quartz | C2 | |
| Gypsum | C3 | J1 |
| Albite | C4 | |
| Anorthite | C5 | |
| Orthoclase | C6 | J2 |
| Apatite | C7 | J3 |
| Halite | C8 | |
| Calcite | C9 | |
| Dolomite | C10 | |
| Na carb | C11 | |
| Siderite | C12 | J4 |
| Biotite | C13 | J5 |
| Muscovite | C14 | |
| Chlorite | C15 | |
| Stilbite | C16 | |
| Pyrite | C17 | J6 |

| Interlayer (Grid #5) | | Octahedral (Grid #4) | | Anions (Grid #8) | | |
|---|---|---|---|---|---|---|
| Na+ | | Al3+ | E1 | O | M1 | |
| Mg2+ | F1 | Fe3+ | E2 | OH | M2 | |
| K+ | F2 | Fe2+ | E3 | Tetrahedral (Grid #3) | | |
| Ca2+ | F3 | Ti4+ | E4 | Al3+ | D1 | |
| | F4 | Mg2+ | E5 | Si4+ | D2 | |
| Mg Inter/Mg Tot(Grid #6) | | Mn2+ | E6 | Fe3+ | D3 | |
| G1 | | | | | | |
| | | | | | D4 | |
| Cations | F5 | | E7 | | D5 | |
| Charge | F6 | | E8 | | | |
| CEC | F7 | | F8 | | | |

| Set Admixtures (Grid #7-cont) | | |
|---|---|---|
| Admix. | wt. % | Suggest |
| Kaolinite | C18 | |
| Hematite | C19 | |
| New | C20 | |
| New | C21 | |
| New | C22 | |
| New | C23 | |
| New | C24 | |
| New | C25 | |
| New | C26 | |
| New | C27 | |
| New | C28 | |
| MnO | C29 | J7 |
| TiO2 | C30 | J8 |
| Cr2O3 | C31 | J9 |
| Total Admixtures | | |
| | H1 | |

FIG. 3

Example #1

| Element | wt. % |
|---|---|
| O | 49.24 |
| Na | 3.79 |
| Mg | 1.86 |
| Al | 11.95 |
| Si | 30.11 |
| P | 0.00 |
| S | 0.01 |
| K | 0.13 |
| Ca | 0.10 |
| Ti | 0.14 |
| Cr | 0.00 |
| Mn | 0.01 |
| Fe | 2.62 |
| Total | 99.96 |

Fe2+/(Fe2+Fe3+): 0.2

Set Admixtures

| Admix. | wt. % | Suggest |
|---|---|---|
| Opal-CT | 0.0 | |
| Quartz | 0.0 | |
| Gypsum | 0.0 | 0.05 |
| Albite | 0.0 | |
| Anorthite | 0.0 | |
| Orthoclase | 0.0 | 0.93 |
| Apatite | 0.0 | 0.00 |
| Halite | 0.0 | |
| Calcite | 0.0 | |
| Dolomite | 0.0 | |
| Na carb | 0.0 | |
| Siderite | 0.0 | |
| Biotite | 0.0 | 1.55 |
| Muscovite | 0.0 | 1.33 |
| Chlorite | 0.0 | |
| Stilbite | 0.0 | |
| Pyrite | 0.0 | 0.02 |

Set Admixtures

| Admix. | wt. % | Suggest |
|---|---|---|
| Kaolinite | 0.0 | |
| Hematite | 0.0 | |
| New | 0.0 | |
| New | 0.0 | |
| New | 0.0 | |
| New | 0.0 | |
| New | 0.0 | |
| New | 0.0 | |
| New | 0.0 | |
| New | 0.0 | |
| MnO | 0.0 | 0.01 |
| TiO2 | 0.0 | 0.23 |
| Cr2O3 | 0.0 | 0.00 |
| Total Admixtures | 0.0 | |

Clay Composition

| Oxide | Wt. % | # cat./f.unit |
|---|---|---|
| SiO2 | 64.75 | 3.869 |
| TiO2 | 0.23 | 0.011 |
| Al2O3 | 22.70 | 1.598 |
| Fe2O3 | 3.01 | 0.144 |
| FeO | 0.75 | 0.038 |
| MnO | 0.01 | 0.001 |
| MgO | 3.10 | 0.276 |
| CaO | 0.14 | 0.009 |
| Na2O | 5.14 | 0.595 |
| K2O | 0.16 | 0.012 |
| | 100.00 | 6.553 |

| Interlayer | | Octahedral | | Anions | |
|---|---|---|---|---|---|
| Na+ | 0.595 | Al3+ | 1.468 | O | 10.0 |
| Mg2+ | 0.000 | Fe3+ | 0.144 | OH | 2.0 |
| K+ | 0.012 | Fe2+ | 0.038 | Tetrahedral | |
| Ca2+ | 0.009 | Ti4+ | 0.011 | Al3+ | 0.131 |
| | | Mg2+ | 0.276 | Si4+ | 3.869 |
| Mg Inter/Mg Tot | | Mn2+ | 0.001 | Fe3+ | 0.000 |
| 0.00 | | | | | |
| | | Cations | 0.62 | | 1.94 |
| | | Charge | 0.62 | | 5.51 |
| | | CEC | 172 | | |
| | | | 172 | | 4.00 |
| | | | | | 15.87 |

FIG. 4

Example #1

| Element | wt. % |
|---|---|
| O | 49.24 |
| Na | 3.79 |
| Mg | 1.86 |
| Al | 11.95 |
| Si | 30.11 |
| P | 0.00 |
| S | 0.01 |
| K | 0.13 |
| Ca | 0.10 |
| Ti | 0.14 |
| Cr | 0.00 |
| Mn | 0.01 |
| Fe | 2.62 |
| Total | 99.96 |

| $Fe^{2+}/(Fe^{2+}+Fe^{3+})$ |
|---|
| 0.2 |

Set Admixtures

| Admix. | wt. % | Suggest |
|---|---|---|
| Opal-CT | 0.0 | |
| Quartz | 1.5 | |
| Gypsum | 0.0 | 0.05 |
| Albite | 0.0 | |
| Anorthite | 0.0 | |
| Orthoclase | 0.0 | 0.93 |
| Apatite | 0.0 | 0.00 |
| Halite | 0.0 | |
| Calcite | 0.0 | |
| Dolomite | 0.0 | |
| Na carb | 0.0 | |
| Siderite | 0.0 | |
| Biotite | 0.0 | 1.55 |
| Muscovite | 0.0 | 1.33 |
| Chlorite | 0.0 | |
| Stilbite | 0.0 | |
| Pyrite | 0.0 | 0.02 |

Set Admixtures

| Admix. | wt. % | Suggest |
|---|---|---|
| Kaolinite | 0.0 | |
| Hematite | 0.0 | |
| New | 0.0 | |
| New | 0.0 | |
| New | 0.0 | |
| New | 0.0 | |
| New | 0.0 | |
| New | 0.0 | |
| New | 0.0 | |
| MnO | 0.0 | 0.01 |
| TiO2 | 0.0 | 0.23 |
| Cr2O3 | 0.0 | 0.00 |
| Total Admixtures | 1.5 | |

Clay Composition

| Oxide | Wt. % | # cat./f.unit |
|---|---|---|
| SiO2 | 64.21 | 3.842 |
| TiO2 | 0.24 | 0.011 |
| Al2O3 | 23.05 | 1.625 |
| Fe2O3 | 3.06 | 0.147 |
| FeO | 0.76 | 0.038 |
| MnO | 0.01 | 0.001 |
| MgO | 3.15 | 0.281 |
| CaO | 0.14 | 0.009 |
| Na2O | 5.21 | 0.605 |
| K2O | 0.16 | 0.012 |
| Total | 100.00 | 6.571 |

| Interlayer | | Octahedral | | Anions | |
|---|---|---|---|---|---|
| Na+ | 0.605 | Al3+ | 1.467 | O | 10.0 |
| Mg2+ | 0.000 | Fe3+ | 0.147 | OH | 2.0 |
| K+ | 0.012 | Fe2+ | 0.038 | Tetrahedral | |
| Ca2+ | 0.009 | Ti4+ | 0.011 | Al3+ | 0.158 |
| | | Mg2+ | 0.281 | Si4+ | 3.842 |
| Mg Inter/Mg Tot | 0.00 | Mn2+ | 0.00 | Fe3+ | 0.000 |
| Cations | 0.63 | | 1.94 | | 4.00 |
| Charge | 0.64 | | 5.52 | | 15.84 |
| CEC | 175 | | 172 | | |

FIG. 5

| Example #1 | |
|---|---|
| Element | wt. % |
| O | 49.24 |
| Na | 3.79 |
| Mg | 1.86 |
| Al | 11.95 |
| Si | 30.11 |
| P | 0.00 |
| S | 0.01 |
| K | 0.13 |
| Ca | 0.10 |
| Ti | 0.14 |
| Cr | 0.00 |
| Mn | 0.01 |
| Fe | 2.62 |
| Total | 99.96 |

| $Fe^{2+}/(Fe^{2+}+Fe^{3+})$ |
|---|
| 0.2 |

| Set Admixtures | | |
|---|---|---|
| Admix. | wt. % | Suggest |
| Opal-CT | 0.0 | |
| Quartz | 1.5 | |
| Gypsum | 0.0 | 0.05 |
| Albite | 0.0 | |
| Anorthite | 0.0 | |
| Orthoclase | 0.0 | 0.93 |
| Apatite | 0.0 | 0.00 |
| Halite | 3.1 | |
| Calcite | 0.0 | |
| Dolomite | 0.0 | |
| Na carb | 0.0 | |
| Siderite | 0.0 | |
| Biotite | 0.0 | 1.55 |
| Muscovite | 0.0 | 1.33 |
| Chlorite | 0.0 | |
| Stilbite | 0.0 | |
| Pyrite | 0.0 | 0.02 |

| Set Admixtures | | |
|---|---|---|
| Admix. | wt. % | Suggest |
| Kaolinite | 0.0 | |
| Hematite | 0.0 | |
| New | 0.0 | |
| New | 0.0 | |
| New | 0.0 | |
| New | 0.0 | |
| New | 0.0 | |
| New | 0.0 | |
| New | 0.0 | |
| MnO | 0.0 | 0.01 |
| TiO2 | 0.0 | 0.23 |
| Cr2O3 | 0.0 | 0.00 |
| Total Admixtures | 4.6 | |

| Clay Composition | | |
|---|---|---|
| Oxide | Wt. % | # cat./f.unit |
| SiO2 | 65.31 | 3.876 |
| TiO2 | 0.24 | 0.011 |
| Al2O3 | 23.44 | 1.640 |
| Fe2O3 | 3.11 | 0.148 |
| FeO | 0.78 | 0.039 |
| MnO | 0.01 | 0.001 |
| MgO | 3.20 | 0.283 |
| CaO | 0.15 | 0.009 |
| Na2O | 3.60 | 0.414 |
| K2O | 0.16 | 0.012 |
| | 100.00 | 6.433 |

| Interlayer | | Octahedral | | Anions | |
|---|---|---|---|---|---|
| Na+ | 0.414 | Al3+ | 1.516 | O | 10.0 |
| Mg2+ | 0.000 | Fe3+ | 0.148 | OH | 2.0 |
| K+ | 0.012 | Fe2+ | 0.039 | Tetrahedral | |
| Ca2+ | 0.009 | Ti4+ | 0.011 | Al3+ | 0.124 |
| | | Mg2+ | 0.283 | Si4+ | 3.876 |
| | | Mn2+ | 0.001 | Fe3+ | 0.000 |
| Mg Inter/Mg Tot | 0.00 | | | | |
| Cations | 0.44 | | 2.00 | | 4.00 |
| Charge | 0.44 | | 5.68 | | 15.88 |
| CEC | 122 | | 116 | | |

FIG. 7

| Example #2 | |
|---|---|
| Element | wt. % |
| O | 48.67 |
| Na | 2.54 |
| Mg | 1.90 |
| Al | 10.42 |
| Si | 30.29 |
| P | 0.00 |
| S | 0.01 |
| K | 0.22 |
| Ca | 0.20 |
| Ti | 0.54 |
| Cr | 0.00 |
| Mn | 0.01 |
| Fe | 5.15 |
| Total | 99.95 |

| Fe2+/(Fe2+Fe3+) |
|---|
| 0.3 |

| Set Admixtures | | |
|---|---|---|
| Admix. | wt. % | Suggest |
| Opal-CT | 0.0 | |
| Quartz | 0.0 | |
| Gypsum | 0.0 | 0.05 |
| Albite | 0.0 | |
| Anorthite | 0.0 | |
| Orthoclase | 0.0 | 1.57 |
| Apatite | 0.0 | 0.00 |
| Halite | 0.0 | |
| Calcite | 0.0 | |
| Dolomite | 0.0 | |
| Na carb | 0.0 | |
| Siderite | 0.0 | |
| Biotite | 0.0 | 2.61 |
| Muscovite | 0.0 | 2.26 |
| Chlorite | 0.0 | |
| Stilbite | 0.0 | |
| Pyrite | 0.0 | 0.02 |

| Set Admixtures | | |
|---|---|---|
| Admix. | wt. % | Suggest |
| Kaolinite | 0.0 | |
| Hematite | 0.0 | |
| New | 0.0 | |
| New | 0.0 | |
| New | 0.0 | |
| New | 0.0 | |
| New | 0.0 | |
| New | 0.0 | |
| New | 0.0 | |
| New | 0.0 | |
| MnO | 0.0 | 0.01 |
| TiO2 | 0.0 | 0.89 |
| Cr2O3 | 0.0 | 0.00 |
| Total Admixtures | 0.0 | |

| Clay Composition | | |
|---|---|---|
| Oxide | Wt.% | # cat./ f.unit |
| SiO2 | 64.87 | 3.908 |
| TiO2 | 0.90 | 0.041 |
| Al2O3 | 19.71 | 1.399 |
| Fe2O3 | 5.46 | 0.264 |
| FeO | 1.92 | 0.097 |
| MnO | 0.01 | 0.001 |
| MgO | 3.15 | 0.283 |
| CaO | 0.28 | 0.018 |
| Na2O | 3.43 | 0.400 |
| K2O | 0.27 | 0.020 |
| | 100.00 | 6.431 |

| Interlayer | | Octahedral | | Anions | |
|---|---|---|---|---|---|
| Na+ | 0.400 | Al3+ | 1.307 | O | 10.0 |
| Mg2+ | 0.000 | Fe3+ | 0.264 | OH | 2.0 |
| K+ | 0.020 | Fe2+ | 0.097 | Tetrahedral | |
| Ca2+ | 0.018 | Ti4+ | 0.041 | Al3+ | 0.092 |
| | | Mg2+ | 0.283 | Si4+ | 3.908 |
| Mg Inter/Mg Tot | | Mn2+ | 0.001 | Fe3+ | 0.000 |
| 0.00 | | | | | |
| Cations | 0.44 | | 1.99 | | 4.00 |
| Charge | 0.46 | | 5.64 | | 15.91 |
| CEC | 123 | | 123 | | |

FIG. 8

| Example #2 | |
|---|---|
| Element | wt.% |
| O | 48.67 |
| Na | 2.54 |
| Mg | 1.90 |
| Al | 10.42 |
| Si | 30.29 |
| P | 0.00 |
| S | 0.01 |
| K | 0.22 |
| Ca | 0.20 |
| Ti | 0.54 |
| Cr | 0.00 |
| Mn | 0.01 |
| Fe | 5.15 |
| Total | 99.95 |

| Fe2+/(Fe2+Fe3+) |
|---|
| 0.3 |

| Set Admixtures | | |
|---|---|---|
| Admix. | wt.% | Suggest |
| Opal-CT | 0.0 | |
| Quartz | 0.0 | |
| Gypsum | 0.0 | 0.05 |
| Albite | 0.0 | |
| Anorthite | 0.0 | |
| Orthoclase | 1.0 | 1.57 |
| Apatite | 0.0 | 0.00 |
| Halite | 0.0 | |
| Calcite | 0.1 | |
| Dolomite | 0.0 | |
| Na carb | 0.0 | |
| Siderite | 0.0 | |
| Biotite | 0.0 | 2.61 |
| Muscovite | 0.0 | 2.26 |
| Chlorite | 0.0 | |
| Stilbite | 0.0 | |
| Pyrite | 0.0 | 0.02 |

| Set Admixtures | | |
|---|---|---|
| Admix. | wt.% | Suggest |
| Kaolinite | 0.0 | |
| Hematite | 0.0 | |
| New | 0.0 | |
| New | 0.0 | |
| New | 0.0 | |
| New | 0.0 | |
| New | 0.0 | |
| New | 0.0 | |
| New | 0.0 | |
| MnO | 0.0 | 0.01 |
| TiO2 | 0.0 | 0.89 |
| Cr2O3 | 0.0 | 0.00 |
| Total Admixtures | 1.1 | |

| Clay Composition | | |
|---|---|---|
| Oxide | Wt.% | # cat./f.unit |
| SiO2 | 64.91 | 3.909 |
| TiO2 | 0.91 | 0.041 |
| Al2O3 | 19.74 | 1.401 |
| Fe2O3 | 5.22 | 0.252 |
| FeO | 2.24 | 0.113 |
| MnO | 0.01 | 0.001 |
| MgO | 3.19 | 0.286 |
| CaO | 0.23 | 0.015 |
| Na2O | 3.46 | 0.405 |
| K2O | 0.10 | 0.007 |
| | 100.00 | 6.430 |

| Interlayer | | Octahedral | | Anions | |
|---|---|---|---|---|---|
| Na+ | 0.405 | Al3+ | 1.310 | O | 10.0 |
| Mg2+ | 0.000 | Fe3+ | 0.252 | OH | 2.0 |
| K+ | 0.007 | Fe2+ | 0.113 | Tetrahedral | |
| Ca2+ | 0.015 | Ti4+ | 0.041 | Al3+ | 0.091 |
| | | Mg2+ | 0.286 | Si4+ | 3.909 |
| Mg Inter/Mg Tot | | Mn2+ | 0.001 | Fe3+ | 0.000 |
| 0.00 | | | | | |
| | | Cations | 2.00 | | 4.00 |
| | | Charge | 0.44 | | 15.91 |
| | | CEC | 118 | | |

FIG. 10

| Example #3 | |
|---|---|
| Element | wt. % |
| O | 50.46 |
| Na | 1.81 |
| Mg | 1.55 |
| Al | 8.91 |
| Si | 34.85 |
| P | 0.00 |
| S | 0.06 |
| K | 0.34 |
| Ca | 0.19 |
| Ti | 0.11 |
| Cr | 0.00 |
| Mn | 0.02 |
| Fe | 1.68 |
| Total | 99.98 |

| $Fe^{2+}/(Fe^{2+}+Fe^{3+})$ |
|---|
| 0.1 |

| Set Admixtures | | |
|---|---|---|
| Admix. | wt. % | Suggest |
| Opal-CT | 0.0 | |
| Quartz | 0.0 | |
| Gypsum | 0.0 | 0.32 |
| Albite | 0.0 | |
| Anorthite | 0.0 | |
| Orthoclase | 0.0 | 2.42 |
| Apatite | 0.0 | 0.00 |
| Halite | 0.0 | |
| Calcite | 0.0 | |
| Dolomite | 0.0 | |
| Na carb | 0.0 | |
| Siderite | 0.0 | |
| Biotite | 0.0 | 4.04 |
| Muscovite | 0.0 | 3.49 |
| Chlorite | 0.0 | |
| Stilbite | 0.0 | |
| Pyrite | 0.0 | 0.11 |

| Set Admixtures | | |
|---|---|---|
| Admix. | wt. % | Suggest |
| Kaolinite | 0.0 | |
| Hematite | 0.0 | |
| New | 0.0 | |
| New | 0.0 | |
| New | 0.0 | |
| New | 0.0 | |
| New | 0.0 | |
| New | 0.0 | |
| New | 0.0 | |
| MnO | 0.0 | 0.03 |
| TiO2 | 0.0 | 0.18 |
| Cr2O3 | 0.0 | 0.00 |
| Total Admixtures | 0.0 | |

| Clay Composition | | |
|---|---|---|
| Oxide | Wt. % | # cat./f.unit |
| SiO2 | 74.78 | 4.346 |
| TiO2 | 0.18 | 0.008 |
| Al2O3 | 16.89 | 1.157 |
| Fe2O3 | 2.17 | 0.101 |
| FeO | 0.24 | 0.012 |
| MnO | 0.03 | 0.001 |
| MgO | 2.58 | 0.223 |
| CaO | 0.27 | 0.017 |
| Na2O | 2.45 | 0.276 |
| K2O | 0.41 | 0.030 |
| | 100.00 | 6.172 |

| Interlayer | | Octahedral | | Anions | |
|---|---|---|---|---|---|
| Na+ | 0.276 | Al3+ | | O | 10.0 |
| Mg2+ | 0.000 | Fe3+ | | OH | 2.0 |
| K+ | 0.030 | Fe2+ | | Tetrahedral | |
| Ca2+ | 0.017 | Ti4+ | | Al3+ | 0.000 |
| | | Mg2+ | | Si4+ | 4.346 |
| Mg Inter/Mg Tot | | Mn2+ | | Fe3+ | 0.000 |
| 0.00 | | | | | |
| | | | | | 4.35 |
| Cations | 0.32 | | 1.50 | | 17.38 |
| Charge | 0.34 | | 4.28 | | |
| CEC | 95 | | 95 | | |

FIG. 11

| Example #3 | |
|---|---|
| Element | wt. % |
| O | 50.46 |
| Na | 1.81 |
| Mg | 1.55 |
| Al | 8.91 |
| Si | 34.85 |
| P | 0.00 |
| S | 0.06 |
| K | 0.34 |
| Ca | 0.19 |
| Ti | 0.11 |
| Cr | 0.00 |
| Mn | 0.02 |
| Fe | 1.68 |
| Total | 99.98 |

| Fe2+/(Fe2+Fe3+) |
|---|
| 0.1 |

| Set Admixtures | | |
|---|---|---|
| Admix. | wt. % | Suggest |
| Opal-CT | 15.0 | |
| Quartz | 0.0 | |
| Gypsum | 0.3 | 0.32 |
| Albite | 0.0 | |
| Anorthite | 0.0 | |
| Orthoclase | 2.4 | 2.42 |
| Apatite | 0.0 | 0.00 |
| Halite | 0.0 | |
| Calcite | 0.0 | |
| Dolomite | 0.0 | |
| Na carb | 0.0 | |
| Siderite | 0.0 | |
| Biotite | 0.0 | 4.04 |
| Muscovite | 0.0 | 3.49 |
| Chlorite | 0.0 | |
| Stilbite | 0.0 | |
| Pyrite | 0.0 | 0.11 |

| Set Admixtures | | |
|---|---|---|
| Admix. | wt. % | Suggest |
| Kaolinite | 0.0 | |
| Hematite | 0.0 | |
| New | 0.0 | |
| New | 0.0 | |
| New | 0.0 | |
| New | 0.0 | |
| New | 0.0 | |
| New | 0.0 | |
| New | 0.0 | |
| New | 0.0 | |
| MnO | 0.0 | 0.03 |
| TiO2 | 0.0 | 0.18 |
| Cr2O3 | 0.0 | 0.00 |
| Total Admixtures | 17.7 | |

| Clay Composition | | |
|---|---|---|
| Oxide | Wt. % | # cat./f.unit |
| SiO2 | 70.57 | 4.131 |
| TiO2 | 0.22 | 0.010 |
| Al2O3 | 19.95 | 1.376 |
| Fe2O3 | 2.64 | 0.124 |
| FeO | 0.29 | 0.014 |
| MnO | 0.03 | 0.002 |
| MgO | 3.13 | 0.273 |
| CaO | 0.20 | 0.013 |
| Na2O | 2.97 | 0.337 |
| K2O | 0.00 | 0.000 |
| | 100.00 | 6.280 |

| Interlayer | | | Octahedral | | | Anions | |
|---|---|---|---|---|---|---|---|
| Na+ | 0.337 | | Al3+ | 1.376 | | O | 10.0 |
| Mg2+ | 0.000 | | Fe3+ | 0.124 | | OH | 2.0 |
| K+ | 0.000 | | Fe2+ | 0.014 | | Tetrahedral | |
| Ca2+ | 0.013 | | Ti4+ | 0.010 | | Al3+ | 0.000 |
| | | | Mg2+ | 0.273 | | Si4+ | 4.131 |
| Mg Inter/Mg Tot | | | Mn2+ | 0.002 | | Fe3+ | 0.000 |
| | 0.00 | | | | | | |
| Cations | 0.35 | | | 1.80 | | | 4.13 |
| Charge | 0.36 | | | 5.12 | | | 16.52 |
| CEC | 100 | | | 82 | | | |

FIG. 12

| Example #3 | |
|---|---|
| Element | wt. % |
| O | 50.46 |
| Na | 1.81 |
| Mg | 1.55 |
| Al | 8.91 |
| Si | 34.85 |
| P | 0.00 |
| S | 0.06 |
| K | 0.34 |
| Ca | 0.19 |
| Ti | 0.11 |
| Cr | 0.00 |
| Mn | 0.02 |
| Fe | 1.68 |
| Total | 99.98 |

| Set Admixtures | | |
|---|---|---|
| Admix. | wt. % | Suggest |
| Opal-CT | 25.5 | |
| Quartz | 0.0 | |
| Gypsum | 0.3 | 0.32 |
| Albite | 0.0 | |
| Anorthite | 0.0 | |
| Orthoclase | 2.4 | 2.42 |
| Apatite | 0.0 | 0.00 |
| Halite | 0.0 | |
| Calcite | 0.0 | |
| Dolomite | 0.0 | |
| Na carb | 0.0 | |
| Siderite | 0.0 | |
| Biotite | 0.0 | 4.04 |
| Muscovite | 0.0 | 3.49 |
| Chlorite | 0.0 | |
| Stilbite | 0.0 | |
| Pyrite | 0.0 | 0.11 |

| Set Admixtures | | |
|---|---|---|
| Admix. | wt. % | Suggest |
| Kaolinite | 0.0 | |
| Hematite | 0.0 | |
| New | 0.0 | |
| New | 0.0 | |
| New | 0.0 | |
| New | 0.0 | |
| New | 0.0 | |
| New | 0.0 | |
| New | 0.0 | |
| MnO | 0.0 | 0.03 |
| TiO2 | 0.0 | 0.18 |
| Cr2O3 | 0.0 | 0.00 |
| Total Admixtures | 28.3 | |

| Fe2+/(Fe2+Fe3+) |
|---|
| 0.1 |

| Clay Composition | | |
|---|---|---|
| Oxide | Wt. % | # cat./f.unit |
| SiO2 | 66.26 | 3.915 |
| TiO2 | 0.25 | 0.011 |
| Al2O3 | 22.87 | 1.593 |
| Fe2O3 | 3.02 | 0.144 |
| FeO | 0.34 | 0.017 |
| MnO | 0.04 | 0.002 |
| MgO | 3.59 | 0.316 |
| CaO | 0.23 | 0.015 |
| Na2O | 3.40 | 0.390 |
| K2O | 0.00 | 0.000 |
| | 100.00 | 6.402 |

| Interlayer | | Octahedral | | Anions | |
|---|---|---|---|---|---|
| Na+ | 0.390 | Al3+ | 1.508 | O | 10.0 |
| Mg2+ | 0.000 | Fe3+ | 0.144 | OH | 2.0 |
| K+ | 0.000 | Fe2+ | 0.017 | Tetrahedral | |
| Ca2+ | 0.015 | Ti4+ | 0.011 | Al3+ | 0.085 |
| | | Mg2+ | 0.316 | Si4+ | 3.915 |
| Mg Inter/Mg Tot | | Mn2+ | 0.002 | Fe3+ | 0.000 |
| 0.00 | | | | | |
| | | | | | |
| Cations | 0.40 | | 2.00 | | 4.00 |
| Charge | 0.42 | | 5.67 | | 15.92 |
| CEC | 115 | | 83 | | |

METHOD OF DETERMINING THE COMPOSITION OF CLAY DEPOSIT

FIELD OF THE INVENTION

The present invention is directed to a method for selecting a clay deposit, particularly useful for selecting clay deposits that can be purified into a polymer-grade clay for use in nanocomposites. More particularly, the present invention is directed to a method of determining the composition of a clay deposit including the type and amount of crystalline impurities, such as quartz and feldspar, as well as amorphous impurities, such as amorphous silica, to determine if the clay impurities can be separated such that the purified clay includes 5% by weight or less impurities, preferably 3% by weight or less, more preferably 2% by weight or less of impurities.

BACKGROUND OF THE INVENTION AND PRIOR ART

It is well known that layered materials, such as phyllosilicates, can be separated or exfoliated into their individual clay platelets, as disclosed in this assignee's U.S. Pat. Nos. 5,552,469; 5,578,672; and 5,698,624. The exfoliated platelets are useful as fillers for polymeric materials to achieve increases in strength, temperature resistance, gas impermeability, and other properties. While the technology has existed for many years for exfoliating clay platelets and combining such clay platelets with polymeric materials, this technology has not been commercialized, for one reason, among others, that while the addition of exfoliated clay platelets to the polymeric materials has substantially enhanced one or more properties of the polymer, the addition of clay impurities together with the exfoliated platelets has caused a marginal improvement, or has actually caused a decrease in properties that the platelets are designed to increase. Thus far, it has been impossible to sufficiently purify a layered material, such as a phyllosilicate, particularly a smectite clay, such that exfoliated platelets obtained from the purified clay are sufficiently free from clay impurities to significantly enhance the desired properties of the polymer.

Prior attempts to purify a layered material, such as a smectite clay, have included the step of analyzing the clay, such as by x-ray fluorescence, to deterine an elemental analysis of the clay, and then analyzing the clay, such as by an x-ray diffraction (XRD) analysis, in order to identify existing crystalline impurities. These impurities, such as feldspar, quartz and the like can be separated from the smectite clay deposit using well-known physical separation techniques, such as one or more hydrocyclones or a centrifuge. It has been found that identification of crystalline impurities by a technique such as x-ray diffraction is insufficient since it has been found that clay deposits, particularly smectite clay deposits, such as sodium montmorillonite and/or calcium montmorillonite, may include a substantial proportion of amorphous impurities, such as amorphous silica, which cannot be identified by x-ray diffraction. Also, it has been found that using existing technology, it is commercially and/or economically extremely difficult to separate any impurity, e.g., amorphous silica or crystalline impurities, if the impurity is present in the clay deposit in a particle size of five microns or less, particularly less than about one micron.

Thus, there exists a need in the art for a method of identifying clay compositions that include crystalline and amorphous impurities, particularly amorphous silica, within the clay compositions. In accordance with the present invention, it has been found that by using a combination of a means to identify the crystalline components of a clay deposit, such as x-ray diffraction and x-ray fluorescence, together with a means for determining amorphous impurities, which requires a knowledge of crystalline chemistry and mineralogy or clay structure, the components of the clay composition can be determined, including the amount and type of amorphous impurities, particularly amorphous silica impurities, such that the composition of a clay deposit can be determined, accurately, prior to purification of the clay.

SUMMARY OF THE INVENTION

In brief, the present invention is directed to a method of identifying montmorillonite clay-containing compositions and non-montmorillonite clay impurities that are purifiable such that the purified montmorillonite clay has impurities in an amount of less than about 5% by weight, preferably less than about 2% by weight, more preferably less than about 1% by weight. Impurities, in accordance with a preferred embodiment of the present invention, are hereby defined as any material that is not a smectite clay.

Accordingly, one aspect of the present invention is to provide a method of determining an identity and amount of non-smectite clay impurities, both crystalline and amorphous, contained in a clay sample that contains predominantly smectite clay, particularly montmorillonite clay.

Another aspect of the present invention is to provide a method of analyzing a predominantly montmorillonite clay sample to determine a source of Si detected in the sample and, more particularly, to what degree the Si detected is from the montmorillonite clay, or from a non-montmorillonite impurity.

Another aspect of the present invention is to provide a method of analyzing a predominantly montmorillonite clay sample to determine a source of $SiO_2$ detected in the sample and, more particularly, to what degree the $SiO_2$ detected is from the montmorillonite clay, or from a non-montmorillonite impurity.

Another aspect of the present invention is to provide an iterative method of analyzing a predominantly montmorillonite clay sample that includes the steps of analyzing the sample for number of $Si^{+4}$ cations per montmorillonite formula unit, first assuming that all of the $Si^{+4}$ cations are derived from $SiO_2$ contained in the montmorillonite clay contained in the sample; calculating the $Si^{+4}$ per montmorillonite formula unit, and if the number of $Si^{+4}$ cations per formula unit is greater than 4.0, based on the assumption that all $Si^{+4}$ is montmorillonite-derived, reducing the number of $Si^{+4}$ cations per montmorillonite formula unit to a number between 3.8 and 4.0—the quantity of the reduction of the $Si^{+4}$ cations being proportional to the $Si^{+4}$ cations contained in non-montmorillonite impurities contained in the sample.

Still another aspect of the present invention is to calculate the number of $Si^{+4}$ cations contained in non-montmorillonite impurities, as above, and analyzing the clay for $Si^{+4}$-containing crystalline impurities, such as by x-ray diffraction—the difference being proportional to the amount of amorphous impurities containing $Si^{+4}$.

Another aspect of the present invention is to provide an iterative method of analyzing a predominantly montmorillonite clay sample for composition, including impurities, that includes the steps of analyzing the sample for number of $Si^{+4}$ cations per montmorillonite formula unit, first assuming that all of the $Si^{+4}$ cations are derived from $SiO_2$ contained in the montmorillonite clay contained in the sample; calculating the weight percent of $SiO_2$ in the sample, and number of $Si^{+4}$ cations per montmorillonite formula unit, and if the number of $Si^{+4}$ cations per formula unit is greater than 4.0, based on the assumption that all $SiO_2$ is montmorillonite-derived, reducing the weight percent of montmorillonite-derived $SiO_2$—the quantity of the reduction of the montmorillonite-derived $SiO_2$ weight percent being proportional to the weight percent of $SiO_2$ contained in non-montmorillonite impurities contained in the sample.

Still another aspect of the present invention is to provide a method of determining the composition of a clay sample that includes the step of calculating the weight percent of $SiO_2$ contained in non-montmorillonite impurities, as above, and analyzing the clay for $SiO_2$-containing crystalline impurities, such as by x-ray diffraction, and calculating a reduced weight percent of montmorillonite-contained $SiO_2$ that provides 3.8 to 4.0 $Si^{+4}$ cations in the tetrahedral clay layer—the difference being the amount of amorphous impurities containing $SiO_2$.

Another aspect of the present invention is to provide a method of determining a quantity and identity of interlayer cations in a predominantly montmorillonite clay sample, particularly $Ca^{+2}$, $Na^+$, and $K^+$ cations, said clay sample including one or more non-montmorillonite impurities containing Ca, Na and/or K, by analyzing the sample to determine the weight percent of Ca, Na and K in the clay sample; assuming that all of Ca, Na and K detected are derived from the montmorillonite clay, and assigning the detected Ca, Na and K to the interlayer of montmorillonite, as number of $Ca^{+2}$, $Na^+$ and $K^+$ cations per montmorillonite formula unit; comparing the total assigned number of montmorillonite interlayer cations per formula unit to the cation exchange capacity of the clay; and lowering the total number of $Ca^{+2}$, $Na^+$, and $K^+$ cations assigned to the montmorillonite interlayer until the assigned interlayer cations correspond with a cation exchange capacity in the range of 90 to 145.

Another aspect of the present invention is to provide a method of analyzing a clay sample for composition that estimates impurities that do not appear in an XRD pattern, or appear incompletely in an XRD pattern, by suggesting an amount of each impurity based on an elemental analysis that includes weight percents of elements that are not contained in the clay formula.

The above and other aspects and advantages of the present invention will become more apparent from the following detailed description of the preferred embodiments, taken in conjunction with the drawings.

BRIEF DESCRIPTION OF THE DRAWINGS

FIG. 1 is a general grid sheet for calculating the mineralogical components of a montmorillonite clay-containing composition and impurities;

FIG. 3 is a grid sheet showing the elemental analysis for the clay of Example 1, as well as the weight percent of oxides (clay composition) calculated from the elemental analysis (assuming no impurities); layer cations; calculated cation exchange (CEC), based on the initial assignment of layer cations; and potential impurities (set admixtures);

FIG. 4 is a grid sheet for the clay composition of Example 1, similar to FIG. 3, containing revised calculations, based on 1.5% quartz impurity found in the XRD pattern of FIG. 2;

FIG. 5 is a grid sheet, similar to FIGS. 3 and 4, showing the final composition for the clay of Example 1;

FIG. 7 is a grid sheet showing the elemental analysis for the clay of Example 2, as well as the weight percent of oxides (clay composition) calculated from the elemental analysis (assuming no impurities); layer cations; calculated cation exchange (CEC), based on the initial assignment of layer cations; and potential impurities (set admixtures);

FIG. 8 is a grid sheet for the clay composition of Example 2, similar to FIG. 7, containing revised (final) composition calculations, based on 1.0% orthoclase impurity found in the XRD pattern of FIG. 6;

FIG. 10 is a grid sheet showing the elemental analysis for the clay of Example 3, as well as the weight percent of oxides (clay composition) calculated from the elemental analysis (assuming no impurities); layer cations; calculated cation exchange (CEC), based on the initial assignment of layer cations; and potential impurities (set admixtures);

FIG. 11 is grid sheet for the clay composition of Example 3, similar to FIG. 10, containing revised calculations, based on 15.0% opal-CT, 2.4% orthoclase-and 0.3% gypsum impurities found in the XRD pattern of FIG. 9;

FIG. 12 is a grid sheet, similar to FIGS. 10 and 11, showing the final composition for the clay of Example 3.

DETAILED DESCRIPTION OF THE PREFERRED EMBODIMENTS

Figure 2:
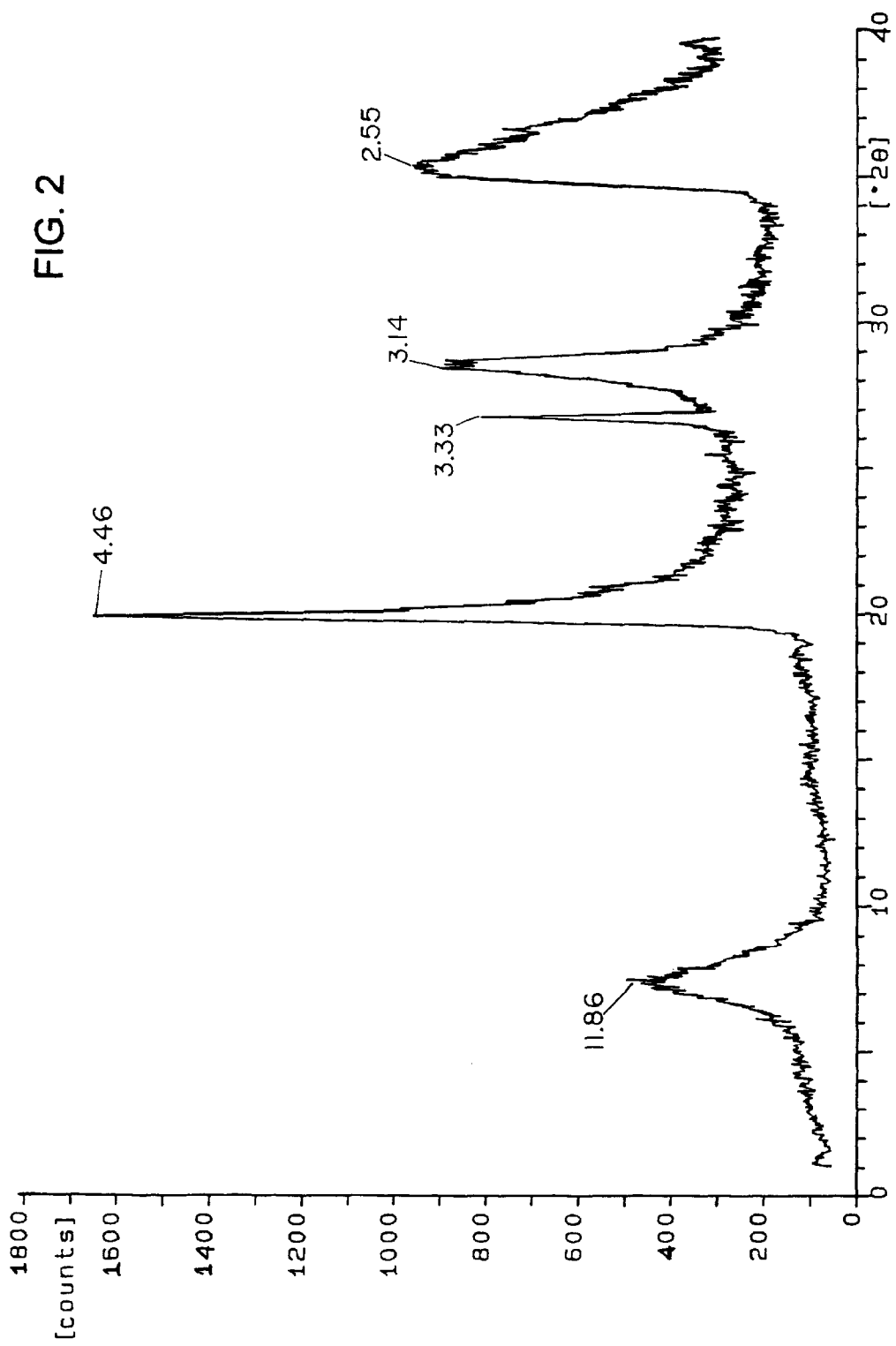
FIG. 2 is an x-ray diffraction (XRD) pattern for the clay composition of Example 1.

In accordance with the present invention, it has been discovered that a preliminary analysis of a representative clay sample will provide an early indication of whether or not the clay sample is suitable as a polymer-grade clay for use in nanocomposites (or if the clay sample is incapable of sufficient purification for use as a polymer-grade clay for use in nanocomposites). This preliminary indication of clay suitability is extremely important in clay selection and to avoid the wasted costs of purifying a clay deposit which is impossible to sufficiently purify for use as a polymer-grade clay for use in nanocomposites. The following clay analysis used to determine an approximate, but relatively exact composition of a clay deposit is very useful in initially determining whether or not the clay deposit is capable of the degree of purification needed for a polymer-grade clay.

As set forth in more detail throughout this specification, polymer-grade clay should have less than about 5% by weight non-smectite impurities, preferably less than about 2% by weight non-smectite impurities, including crystalline and amorphous impurities, in order to provide new and unexpected results in enhancement of polymer properties, when combined with the polymer in a nanocomposite composition.

In order to determine the composition of a clay deposit proposed for use in a nanocomposite composition, e.g., as a polymer filler in the form of exfoliated clay platelets, the clay is analyzed as follows:

The first step in the clay composition/impurities determination is to determine the elemental analysis of the clay sample, e.g., by x-ray fluorescence, to determine weight percent of the sample of the following elements: oxygen, sodium, magnesium, aluminum, silica, phosphorous, sulfur, potassium, calcium, titanium, chromium, manganese, and iron. If the clay sample is predominantly montmorillonite, for example, this elemental analysis can be fit into the structural formula for montmorillonite:

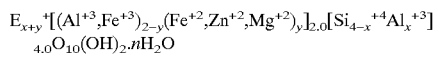
$$E_{x+y}^{+}[(Al^{+3},Fe^{+3})_{2-y}(Fe^{+2},Zn^{+2},Mg^{+2})_y]_{2.0}[Si_{4-x}^{+4}Al_x^{+3}]_{4.0}O_{10}(OH)_2 \cdot nH_2O$$

wherein E=Na, 0.5 Ca and/or 0.5 Mg, and n=1 to 80 usually:

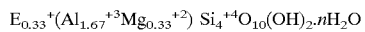
$$E_{0.33}^{+}(Al_{1.67}^{+3}Mg_{0.33}^{+2}) Si_4^{+4}O_{10}(OH)_2 \cdot nH_2O$$

wherein E=Na, 0.5 Ca and/or 0.5 Mg, and n=1 to 80 to determine the weight percent of the following montmorillonite clay components: $SiO_2$, $TiO_2$, $Al_2O_3$, $Fe_2O_3$, FeO, MnO, MgO, CaO, $Na_2O$, and $K_2O$, assuming no impurities. Assuming no impurities, and attempting as closely as possible to fit the elemental analysis into the structural formula for montmorillonite, the percentages for all clay components should add up to about 100% by weight. The actual percentage of these montmorillonite components may change based on a later iterative determination of particular impurities in the sample being analyzed, as will be explained in more detail hereinafter.

From the weight percent of each montmorillonite component, and knowing the molecular weight of each montmorillonite component (oxides), the equivalent weight of each montmorillonite component is determined. For example, at 65.31 weight percent $SiO_2$ in the clay composition (molecular weight of $SiO_2$=60.084), the equivalent weight of $SiO_2$=15.021—the molecular weight of $SiO_2$ divided by the 4 valence of $Si^{+4}$. From these calculations, the gram equivalence of $SiO_2$ (or any other montmorillonite component) per charge is calculated by dividing the weight percent of the montmorillonite component, e.g., 65.310% $SiO_2$, by its equivalent weight (15.02) to obtain gram equivalence of $SiO_2$ per charge of 4.348 for 65.31 weight percent $SiO_2$.

A normalization factor is obtained for each montmorillonite component by adding the gram equivalence per charge for all of the montmorillonite components and dividing the total gram equivalence per charge for all montmorillonite components by 22 (the valence of the 11 oxygens in the montmorillonite formula). The normalization factor is the weight percent of each montmorillonite component (oxide) that will be balanced by each valence charge from the oxygens anions. A cation valence per formula unit can be obtained by dividing the gram equivalence per charge of each montmorillonite component by the normalization factor. From the cation valence per formula unit, the number of cations per formula unit contributed by each montmorillonite component can be determined by dividing the cation valence per formula unit by the cation valence of the montmorillonite component (oxide) cation.

In the following Table I (see Example 1—FIG. 5, if the clay sample has a $SiO_2$ weight percent of 65.31 (equivalent weight=15.02), the gram equivalence per charge=4.348, and the cation valence per formula unit for $SiO_2$=15.529. The total gram equivalence per charge contributed by all montmorillonite components divided by 22, or the normalization factor, equals 0.280. The number of cations per formula unit contributed by the $SiO_2$ is 15.529÷4=3.882. These calculations can be carried out on each of the montmorillonite components to determine the number of cations per formula unit contributed by each montmorillonite component, as shown in Table I:

TABLE I

| Mont. Components Oxide | wt. % | Molecular Weight | Eq. Wt. | Gm. Equiv/ Charge | Cat. Val/ f. unit | No. Cat./ f. unit |
|---|---|---|---|---|---|---|
| $SiO_2$ | 65.31 | 60.09 | 15.02 | 4.348 | 15.529 | 3.882 |
| $TiO_2$ | 0.24 | 79.90 | 19.98 | 0.012 | 0.043 | 0.011 |
| $Al_2O_3$ | 23.44 | 101.96 | 16.99 | 1.379 | 4.925 | 1.642 |
| $Fe_2O_3$ | 3.11 | 159.70 | 26.62 | 0.117 | 0.418 | 0.139 |
| FeO | 0.78 | 71.85 | 35.93 | 0.022 | 0.070 | 0.039 |
| MnO | 0.01 | 70.94 | 35.47 | 0.000 | 0.000 | 0.000 |
| MgO | 3.20 | 40.32 | 20.16 | 0.159 | 0.568 | 0.284 |
| CaO | 0.15 | 56.08 | 28.04 | 0.005 | 0.018 | 0.009 |
| $Na_2O$ | 3.60 | 61.98 | 30.99 | 0.116 | 0.414 | 0.414 |
| $K_2O$ | 0.16 | 94.20 | 47.10 | 0.003 | 0.011 | 0.011 |
| | | | | Total/ 22 = 6.161/ 22 = 0.280* | | Total: 6.431 |

*Normalization factor, normalized to 11 oxygens per formula unit (f. unit).

The number of cations per formula unit are then assigned to the various layers of the montmorillonite clay (interlayer, tetrahedral layer, and octahedral layer).

The number of $Si^{+4}$ cations indicated in the column "No. Cat./f. unit" that are assigned to the tetrahedral layer should be between 3.8 and 4.0. If the number of $Si^{+4}$ cations shown in the table is within 3.8–4.0, all of the $Si^{+4}$ cations should be assigned to the tetrahedral layer. If the number of $Si^{+4}$ cations per formula unit is below 3.8, all of the $Si^{+4}$ cations are assigned to the tetrahedral layer ($Si^{+4}$ never appears in the octahedral layer) and the $Al^{+3}$ cations are assigned to both the tetrahedral layer and the octahedral layer such that the total $Si^{+4}$ and $Al^{+3}$ cations assigned to the tetrahedral layer add up to 4.0. If there are insufficient $Al^{+3}$ cations for assignment to both the tetrahedral layer and the octahedral layer, the $Al^{+3}$ cations are assigned first to the tetrahedral layer such that the total of $Si^{+4}$ cations and $Al^{+3}$ cations in the tetrahedral layer are within the range of 3.8 to 4.0. If additional $Al^{+3}$ cations are available, after the total of $Si^{+4}$ and $Al^{+3}$ in the tetrahedral layer=4.0, $Al^{+3}$ cations which have not been assigned to the tetrahedral layer are assigned to the octahedral layer.

The $Fe^{+3}$ cations (from $Fe_2O_3$) are assigned to the octahedral layer; the $Fe^{+2}$ cations (from FeO) are assigned to the octahedral layer; the $Ti^{+4}$ (from $TiO_2$) are assigned to the octahedral layer; and the $Mn^{+2}$ cations (from MnO) are assigned to the octahedral layer. It should be noted at this point that the magnesium, sodium, potassium and calcium each could be in the interlayer space while magnesium could be in the octahedral layer. Usually, the sodium and calcium are assigned to the interlayer space and, if necessary, the quantity and identity of interlayer cations can be directly measured, such as by atomic absorption, or by bleaching out the interlayer cations, to determine whether or not and to what degree magnesium, sodium, potassium and calcium are assigned to the interlayer space in order to assign these cations properly to either the interlayer space or the tetrahedral layer. $Fe^{+3}$, $Fe^{+2}$ are almost always in the octahedral layer, though very seldom $Fe^{+3}$ can be in the tetrahedral layer.

Once the cations are assigned to their respective layers (interlayer, tetrahedral layer, and octahedral layer) the total number of cations in each layer can be added to find a total layer charge for each layer as a check against the cation assignments to each layer in comparison to the cation exchange capacity. The total interlayer charge, in formula units, should be between 0.3 and 0.5 for a montmorillonite clay, usually in the range of 0.35 to 0.45. The cation exchange capacity can be measured for the clay sample, as well known in the art, or can be calculated based on the molecular weight of the clay and the sum of the layer charges, as well known in the art.

The above analysis, thus far, assumes that the clay sample is 100% montmorillonite and has no impurities. This is adjusted based on analysis of the clay for crystalline impurities, such as by x-ray diffraction, that shows peaks at various locations of the diffraction pattern or graph and relative height and volume of the peak giving an estimate of the quantity of each crystalline impurity, such as quartz and feldspar, to provide adjustments in the clay composition (Grid #2). Similarly, the amount and type of amorphous impurities can be determined, particularly amorphous silica, and the amount of impurities can be subtracted from the initial clay composition to determine revised amounts of montmorillonite components useful for resetting the number of cations in each of the clay layers (interlayer, tetrahedral layer, and octahedral layer) to arrive at a final composition of the clay sample, including amounts of crystalline and amorphous impurities. The above procedure will be more readily understood from the following examples.

In the following examples, clay composition and the identity and quantity of impurities are determined using a number of clay composition sheets, such as shown in FIG. 1. Each clay composition sheet includes a number of grids that are numbered for identification and as a general guideline for an ordered explanation of how the clay composition and identity and quantity of impurities are determined. Each grid includes one or more cells where appropriate numbers, e.g., weight percents, are calculated or assumed, and the numbers are inserted into the appropriate cells during the composition/impurity analysis and calculation. The clay composition sheet of FIG. 1 is shown for montmorillonite clay, but other clay composition sheets can be prepared that include other clay components in the elemental analysis (Grid #1) and clay composition (Grid #2) to determine clay composition and impurities of other types of clays.

EXAMPLE 1

An XRD pattern of the montmorillonite evaluated is shown in FIG. 2. A clay composition sheet (FIG. 3) shows the mineralogical components (clay composition) and possible clay impurities, determined from the elemental analysis (e.g., x-ray fluorescence) and XRD pattern. In performing this evaluation, first the bulk chemical composition (elemental analysis) of the sample was entered into cells A1 through A13, with elements being represented in weight percent. The type and quantity of elements can be determined by x-ray fluorescence, or other techniques, as well known in the art. Next, the ratio of $Fe^{+2}$ to total Fe was entered into (Grid #1A) cell B1, as an optional step to confirm placement of $Fe^{+2}$ and $Fe^{+3}$ into the various layers (tetrahedral layer, and octahedral layer). For this sample the ratio was determined to be 0.2. While greater accuracy is achieved by determining the $Fe^{+2}$ to total Fe ratio by an independent method, this is not required, especially for samples having a total Fe content below 3% by weight. Although exceptions exist, typical ratios for most naturally occurring montmorillonites fall between 0.1 and 0.3. Consequently, an assumed value of 0.2 is generally satisfactory.

From the elemental analysis (Grid #1) the weight percents of the montmorillonite components (Grid #2) can be determined, in accordance with the formula for montmorillonite, following the proper stoichiometry for montmorillonite, and assuming that there are no non-montmorillonite impurities, as well known in the art (see x-ray diffraction and the identification and *Analysis of Clay Minerals,* Duane M. Moore and Robert C. Reynolds, Jr., 1989 pp. 160, et seq.).

From the elemental analysis (Grid #1) and weight percent of montmorillonite clay oxides (Grid #2), the number of cations from each of the montmorillonite components is determined, as explained supra, with reference to Table I. From the number of cations per formula unit (Grid #2), Grids #3, #4, and #5 can be completed as follows:

The $Si^{+4}$ cations (3.876 cations) from Grid #2, cell L1, FIG. 5, are assigned to the tetrahedral layer (Grid #3, cell D2) together with $Al^{+3}$ cations from Grid #2, cell L3 such that the total of $Si^{+4}$ and $Al^{+3}$ cations assigned to cells D1 and D2 equal 4.0 (an additional 0.124 $Al^{+3}$ cations are assigned to cell D1 in the tetrahedral layer such that the 3.876 $Si^{+4}$ cations and the 0.124 $Al^{+3}$ cations assigned to the tetrahedral layer equal 4.0). The $Fe^{+3}$ cations from Grid #2, cell L4 can be assigned either to the tetrahedral layer (Grid #3, cell D3) or to the octahedral layer. If there are sufficient $Al^{+3}$ cations (as in this example) such that the total of $Si^{+4}$ and Al+3 cations assigned to cells D1 and D2 equal 4.0, the $Fe^{+3}$ cations should be assigned to the octahedral layer (Grid #4, cell E2) since the tetrahedral layer (Grid #3) prefers $Al^{+3}$ over $Fe^{+3}$. The remaining $Al^{+3}$ cations (from Grid #2, cell E3), not assigned to the tetrahedral layer in Grid #3, cell D1 (1.640 (from Grid #2, cell L3)—0.124 assigned to Grid #3, cell D1=1.526 $Al^{+3}$ cations assigned to the octahedral layer at Grid #4, cell E1). The $Fe^{+2}$ $Ti^{+4}$, $Mg^{+2}$, and $Mn^{+2}$ cations from Grid #2, cells L5, L2, L7, and L6, respectively, (0.039 $Fe^{+2}$, 0.011 $Ti^{+4}$, 0.283 $Mg^{+2}$, and 0.001 $Mn^{+2}$ cations) are assigned to the octahedral layer at Grid #4, cells E3, E4, E5 and E6, respectively, to complete the octahedral layer (Grid #4).

The $Na^+$, $K^+$ and $Ca^{+2}$ interlayer cations (Grid #5, cells F1, F2, F3 and F4) then are completed by assigning the $Na^+$, $K^+$ and $Ca^{+2}$ cations from Grid #2, cells L9, L10 and L8, respectively, to Grid #5, cells F1, F3 and F4, respectively. It should be noted that the $Mg^{+2}$ cations that were assigned to the octahedral layer (Grid #4, cell E5) can be assigned either to the octahedral layer (Grid #4, cell E5), or to the interlayer (Grid #5, cell F2). This can be determined from a laboratory analysis of the interlayer cations, using, for example, an atomic absorption (AA) analysis or by bleaching the interlayer cations out of the clay and doing an elemental analysis, and/or by checking the cation exchange capacity (CEC) of the clay against the predicted CEC or charge of the clay based on the total cations assigned, at this stage of the analysis, to the interlayer.

Before proceeding further it should be noted that at this stage (FIG. 3), after completing Grids #1, #2, #3, #4, #5 and #6, and prior to accounting for non-clay impurities within the sample, the clay composition (indicated by assigned cations in all layers, clay charge and CEC in cells D1–D4, E1–E7, and F1–F8) did not conform to the accepted crystal chemistry for a montmorillonite clay. At this point the sum of tetrahedral cations was 4.00 (cell D4); the sum of octahedral cations was 1.94 (cell E7); the interlayer charge was 0.62; and the cation exchange capacity (CEC) was 172 (cell F7). A total of 4.00 tetrahedral cations is consistent with the montmorillonite structure, but the sum of 1.94 octahedral cations (should be 2.0±0.01); the interlayer charge was 0.62 (should be in the range of 0.3 to 0.5); and a CEC of 172 do not conform to a montmorillonite clay. The CEC should be between 90 and 145, usually 90–140, more typically 115–130.

To continue with the refinement, the XRD pattern (FIG. 2) was evaluated for crystalline non-montmorillonite impurities. The only non-montmorillonite peak observed was that of quartz at 3.33 Å. By integrating the 3.33 Å peak and comparing the peak area to known standards, a quartz content of 1.5% by weight was determined. This value was entered into the impurity Grid #7, cell C2 (FIG. 4). The resulting value for tetrahedral $Si^{+4}$, after subtracting from the montmorillonite clay-derived $Si^{+4}$ due to the presence of $Si^{+4}$ cations derived from quartz, was 3.842 (cells L1 and D2), within the acceptable limits of 3.80 to 4.00. A determination of interlayer cations by Atomic Absorption showed no $Mg^2$ present. Therefore, a value of 0.0 was entered into cell G1, making the value of $Mg^{+2}$ in cell F2 equal to 0.0.

At this point all crystalline impurities were accounted for and the interlayer $Mg^{+2}$ and $Fe^{+2}$ to total Fe ratio had been confirmed by independent methods, e.g., atomic absorption for interlayer cations. However, the sum of octahedral cations was still 1.94 (FIG. 4, cell E7) and the CEC (calculated based on the quantity of cations in the clay layers) was 175 meq/100 g (cell F7), both unacceptable. Since the data suggested an excess of assigned interlayer Na (calculated CEC was too high), some of the interlayer $Na^+$ was removed by attributing excess Na to a NaCl or halite impurity (cell C8), a contaminant commonly showing poor crystallinity and, therefore, difficult or impossible to quantify by XRD. The addition of 3.1% NaCl (halite) by weight brought the composition of the montmorillonite into acceptable limits: 4.00 tetrahedral cations, 2.00 octahedral cations, and a CEC of 122 meq/100 g (FIG. 5). Subsequent analyses of the sample for NaCl revealed an amount equal to 3.02% NaCl by weight. It should be noted that when the calculated CEC is too high, many times it is atributable to non-detectable (by XRD) Na in the sample, atrributable to $Na_2CO_3$ or NaCl. Similarly, if the calculated CEC is too high, it may be attributable to too many $Ca^{+2}$ ions assigned to the interlayer since a non-detectable (by XRD) amount of calcite ($CaCO_3$) is contained in the clay sample.

It should be noted that the impurity Grid #7 (see FIG. 1) includes two columns—the first column used to insert actual weight percents of impurities, and the second column including spaces for impurities that can be suggested, based on the weight percents of all elements listed in Grid #1. Grid #1 of Example 1 shows 0.01 weight percent sulfur, and 0.13% potassium in the clay sample analyzed. Since neither sulfur nor potassium form part of a montmorillonite clay, these elements necessarily are derived from an impurity (which may or may not appear in an XRD pattern). The "suggest" column of Grid #7 is used to insert weight percents of impurities based on the elemental analysis of Grid #1. In this example, 0.01 weight percent of sulfur could be accounted for by the clay composition including about 0.05 weight percent gypsum (Grid #7, cell J1) or by including 0.02 weight percent pyrite (Grid #7, cell J6). If the XRD pattern shows peak heights for both gypsum and pyrite, and of about equal height and area, the suggest column would be modified to show, e.g., about 0.02 weight percent gypsum and about 0.01 for pyrite. Similarly, since the K impurity can be derived from any (or all of) orthoclase, biotite and/or muskovite, the suggest column at Grid #7, cells J2, J4 and J5 each show the weight percent of each which, alone, could account for 0.13 weight percent potassium in the sample. If XRD peaks appear for two or all three of orthoclase, biotite, and/or muskovite, the percentages for each in the "suggest" column will be reduced such that the additive amounts of potassium from all three impurities will account for 0.13 weight percent potassium in the clay sample.

In this sample it was determined that 4.60% by weight of non-clay impurities were present (3.1% halite and 1.5% quartz). The final montmorillonite composition, expressed as weight percent oxides, appears in cells K1–K10 (FIG. 5). The lack of agreement with an acceptable montmorillonite composition after accounting for 1.5% of the crystalline impurity, quartz, facilitated the determination of an additional 3.1% NaCl.

EXAMPLE 2

Figure 6:
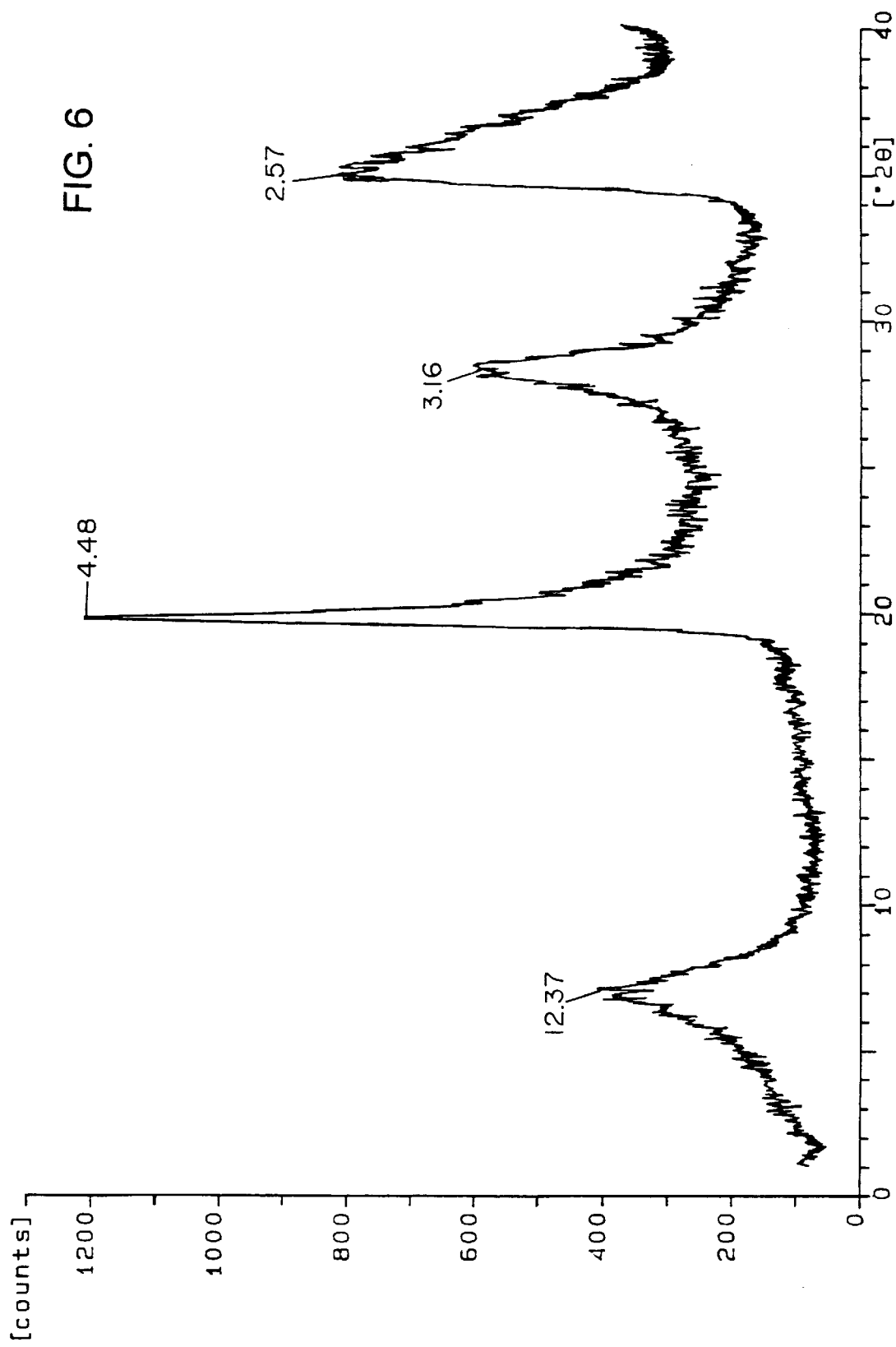
FIG. 6 is an x-ray diffraction (XRD) pattern for the clay composition of Example 2.

In this example, an XRD pattern of the montmorillonite evaluated is shown in FIG. 6. In performing this evaluation, first the elemental analysis (Grid #1, cells A1–A13), and the chemical composition of the sample (Grid #2, cells L1–L10) were entered with elements being represented in weight percent (FIG. 7), as in Example 1, assuming no impurities. The ratio of $Fe^{+2}$ to total Fe was entered into Grid #1A, cell B1. For this sample the ratio was determined to be 0.3.

Even before accounting for non-clay impurities within the sample, the composition (indicated by assigned cations in all layers, clay charge, and CEC in cells D1–D4, E1–E7, and F1–F8) conformed fairly well to the accepted crystal chemistry for a montmorillonite (FIG. 7). At this point, the sum of tetrahedral cations was 4.00 (cell D4), the sum of octahedral cations was 1.99 (cell E7), and the cation exchange capacity (CEC) was 123 meq/100 g (cell F7).

A detailed examination of the XRD pattern (FIG. 6) revealed approximately 1 weight percent orthoclase and 0.1 weight percent calcite. These values were entered into cells C6 and C9, respectively (FIG. 8), and the weight percent of montmorillonite components (Grid #2, cells L1–L10) were adjusted (lowered) to take into account these crystalline impurities. The assigned cations (Grids #3, #4 and #5) were adjusted accordingly. A determination of interlayer cations by Atomic Absorption showed no $Mg^{+2}$ present. Therefore a value of 0.0 was entered into cell G1, making the value of $Mg^{+2}$ in cell F2 equal to 0.0. The resulting value for tetrahedral Si was 3.909 (cell D2), within the acceptable limits of 3.80 to 4.00, the sum of octahedral cations was 2.00 (cell E7), and the cation exchange capacity (CEC) was 119 meq/100 g (cell F7). The final clay composition sheet (FIG. 8) shows the mineralogical components and clay purity determined from the analysis, which has the correct number of $Si^{+4}$ cations per formula unit in the tetrahedral layer (3.909); a correct interlayer charge (0.44); a CEC of 119; 2.00 octahedral cations per formula unit; and 4.00 tetrahedral cations per formula unit.

In this sample it was determined that 1.1% by weight of non-clay impurities were present (1.0% orthoclase and 0.1% calcite). The final montmorillonite composition, expressed as weight percent oxides, appears in cells K1–K10 (FIG. 8). The levels of calcite and orthoclase determined in this example are near the practical detection limits by XRD (because of its greater peak intensity, calcite is detectable at a lower concentration than orthoclase). Because orthoclase is difficult to quantify by XRD, especially at the level of 1%, cell J2 (suggested quantity of the orthoclase impurity) provides an estimate of the orthoclase content of the sample by assuming that all K is associated with orthoclase. Similar estimates are given for the K-bearing minerals biotite (cell J4) and muscovite (cell J5), assuming all $K^+$ ions are derived from biotite or muscovite. Instead of estimating the orthoclase content by XRD, the estimate of 1.57 weight percent provided in cell J2 (based on 0.22 weight percent $K^+$ in the clay sample) could have been used to yield similar results.

EXAMPLE 3

Figure 9:
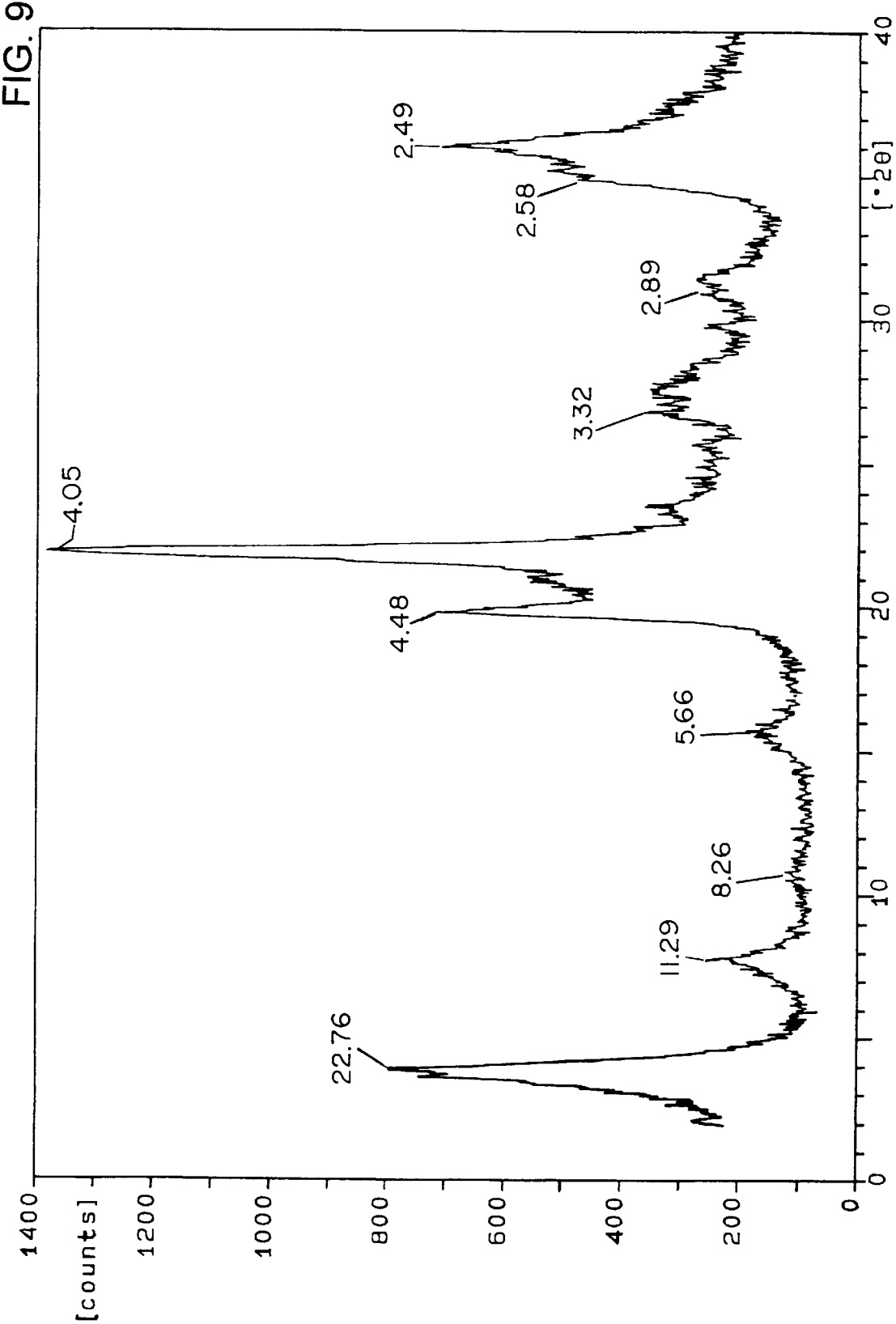
FIG. 9 is an XRD pattern for the clay composition of Example 3.

An XRD pattern of the montmorillonite evaluated is shown in FIG. 9. As in Examples 1 and 2, the elemental analysis is entered in Grid #1 (cells A1–A13) and the chemical composition of the sample was entered into Grid #2 (cells L1–L10) with elements being represented in weight percent. Next, the ratio of $Fe^{+2}$ to total Fe was entered into Grid #1A, cell B1. For this sample the ratio was determined to be 0.1. Using any ratio between 0.0 and 0.3 will give similar results in this example because of low total Fe content.

Prior to accounting for non-clay impurities within the sample, the composition (indicated by assigned cations in all layers, clay charge, and CEC in cells D1–D4, E1–E7, and F1–F8) did not conform to the accepted crystal chemistry of a montmorillonite (FIG. 10). At this point the sum of tetrahedral cations was 4.35 (cell D4), the sum of octahedral cations was 1.50 (cell E7), and the cation exchange capacity (CEC) was 95 meq/100 g (cell F7). A CEC of 95 is acceptable, but a total of 4.35 tetrahedral cations and 1.50 octahedral cations are not.

To continue with the refinement, the XRD pattern (FIG. 9) was evaluated for crystalline non-clay impurities. Approximately 15% Opaline-CT, 2% orthoclase, and a trace of gypsum were identified. As a further refinement of the amounts of orthoclase and gypsum present, the values estimated (based on the elemental analysis of Grid #1) in cells J1 (0.32 weight percent gypsum, based upon 0.06 weight percent sulfur, Grid #1, cell A7) and J2 (2.42 weight percent orthoclase, based upon 0.34 weight percent potassium found in the sample, Grid #1, cell A8) were adopted and entered into cells C3 and C6, respectively (FIG. 11). A value of 15 weight percent Opal-CT was entered into cell C1, based on the XRD pattern. A determination of interlayer cations by Atomic Absorption showed no $Mg^{+2}$ present. Therefore a value of 0.0 was entered into cell G1, making the value of $Mg^{+2}$ in cell F2 equal to 0.0.

After accounting for these impurities (FIG. 11), the value for tetrahedral Si was 4.13 (cell D2), the sum of octahedral cations was 1.80 (cell E7), and the CEC was 100 meq/100 g. The value for the CEC was acceptable, however the values for tetrahedral Si, and the sum of octahedral cations were not. An obvious problem with the montmorillonite composition was the excess of $Si^{+4}$ (cell D2)—the total amount of tetrahedral $Si^{+4}$ in the montmorillonite structure cannot be greater than 4.0. Obtaining a tetrahedral $Si^{+4}$ value outside the range of 3.80 to 4.00 is common for samples high in Opal-CT because the exact amount is difficult to determine by XRD. It has been found that this difficulty is associated with the variation that occurs between the crystalline and amorphous components of Opal-CT (amorphous silica) suggesting that about 10% amorphous silica is contained in the sample (added to Opal-CT in FIG. 12).

To adjust for the excess tetrahedral $Si^{+4}$, the Opal-CT (Grid #7, cell C1—FIG. 11) content was progressively increased (FIG. 12) until the sum of tetrahedral cations was 4.00 (cell D4) and the sum of octahedral cations was 2.00 (cell E7). Whenever the number of $Si^{+4}$ is too high it is usually a result of an amorphous $SiO_2$-containing impurity, such as Opal-CT or feldspar. This procedure yielded an Opal-CT value of 25.5 weight percent in cell C1, FIG. 12, accounted for by amorphous $SiO_2$ that cannot be detected by XRD. The resulting clay composition was in good agreement with the crystal chemistry of montmorillonite (FIG. 12): the sum of tetrahedral cations was 4.00 (cell D4) with Si between 3.80 and 4.00 (cell D2), the sum of octahedral cations was 2.00 (cell E7), and the CEC was 115 meq/100 g (cell F7).

In this sample it was determined that 28.2w by weight of non-clay impurities were present (25.5% opal-CT; 0.3% gypsum; and 2.4% orthoclase). This example illustrates the difficulty of estimating the purity of a sample by XRD alone. By using XRD data for the qualitative identification of Opal-CT and XRD data to reconcile the elemental composition (Grid #1) and montmorillonite component percentages (Grid #2) with an acceptable composition for montmorillonite, a reliable estimate of the total non-clay fraction was obtained.

In accordance with the purification process of the present invention, if the clay sample contains more than about 40% by weight amorphous silica, it will be extremely difficult to remove sufficient amorphous silica and other impurities such that the purified clay has less than about 2% by weight total impurities. In accordance with a preferred embodiment of the present invention, an x-ray diffraction analysis of the clay sample provides identification of crystalline components. Typical crystalline impurities include quartz ($SiO_2$), feldspar ($KAlSi_3O_8$), opal-CT ($SiO_2$); gypsum ($CaSO_4.2H_2O$); albite ($NaAlSi_3O_8$); anorthite ($CaAl_{12}Si_2O_8$); orthoclase ($KAlSi_3O_8$); apatite ($Ca_5(PO_4)_3$ (F, Cl, OH)); halite (NaCl); calcite ($CaCO_3$); dolomite ($CaMg(CO_3)_2$; sodium carbonate ($Na_2CO_3$); siderite ($FeCo_3$) biotite ($K(Mg,Fe)_3(AlSi_3O_{10})(OH)_2$); muscovite ($KAl_2(AlSi_3O_{10})(OH)_2$); chlorite ($(Mg,Fe)_6(Si,Al)_4O_{10}(OH)_8$); stilbite ($NaCa_2Al_5Si_{13}O_{36}.14H_2O$); pyrite ($FeS_2$); kaolinite ($Al_2Si_2O_5.(OH)_4$); and hematite ($Fe_2O_3$).

The crystalline impurities are relatively easy to identify by x-ray diffraction and to separate from the smectite clay by settling, centrifugation, and like physical separation methods, such as filtration. Prior art purification methods have included the step of analyzing a clay sample using x-ray diffraction for identification of crystalline impurities but have not analyzed the clay samples for amorphous impurities, such as amorphous silica. In accordance with the present invention, the clay sample is then analyzed to determine the amorphous impurities in the clay sample, using the iterative techniques disclosed herein combined with known information of crystalline chemistry and mineralogy, and the results from both the means for determining crystalline components, such as x-ray diffraction, and the means for determining amorphous impurities, preferably using an associated computer program, are described in more detail hereinafter, to determine the amount and types of impurities contained in the clay sample.

Figure 13A:
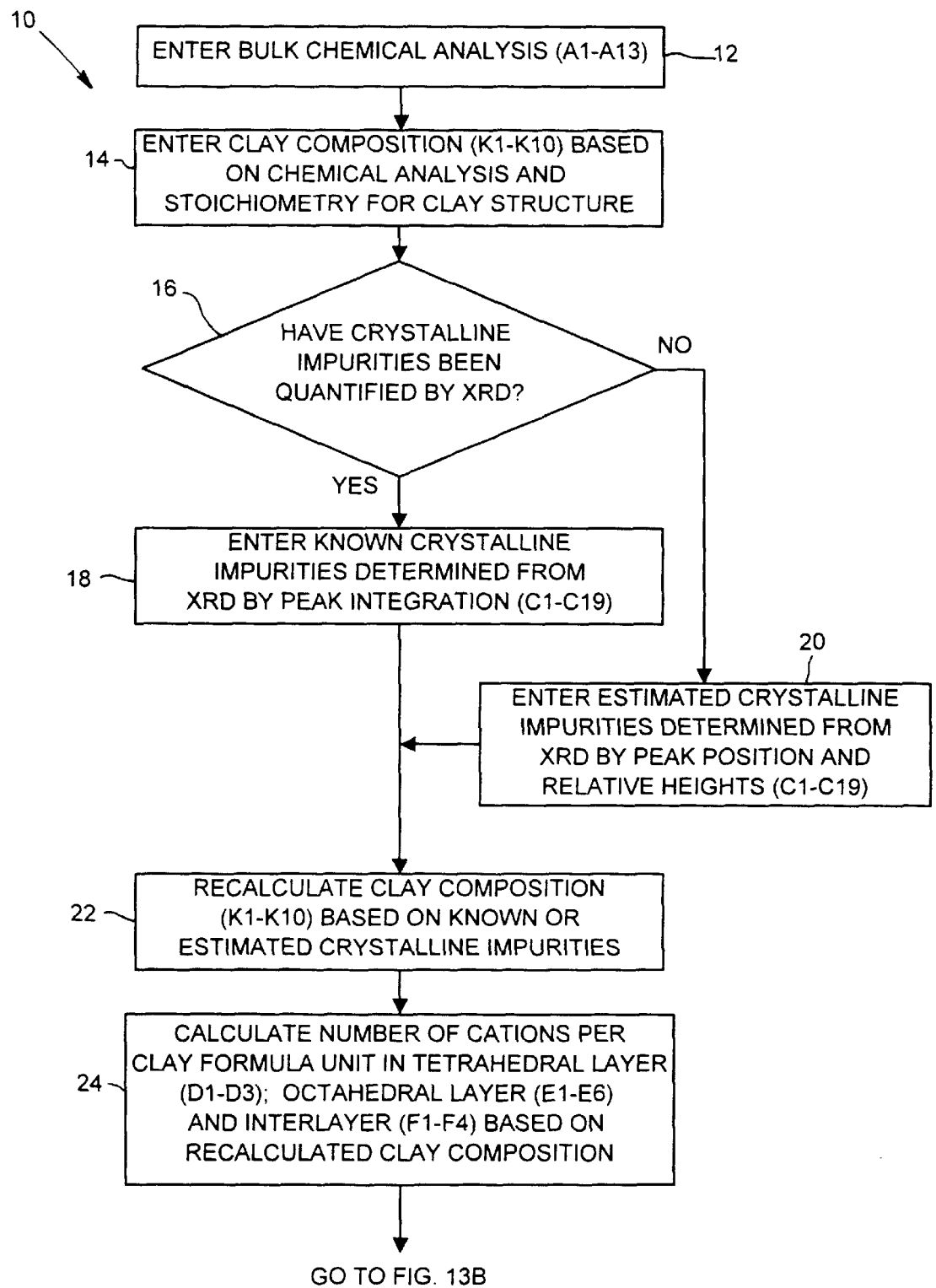
FIGS. 13A–C is a flow chart of an overall, computer-assisted embodiment of the clay composition analysis process of the present invention.
Figure 13B:
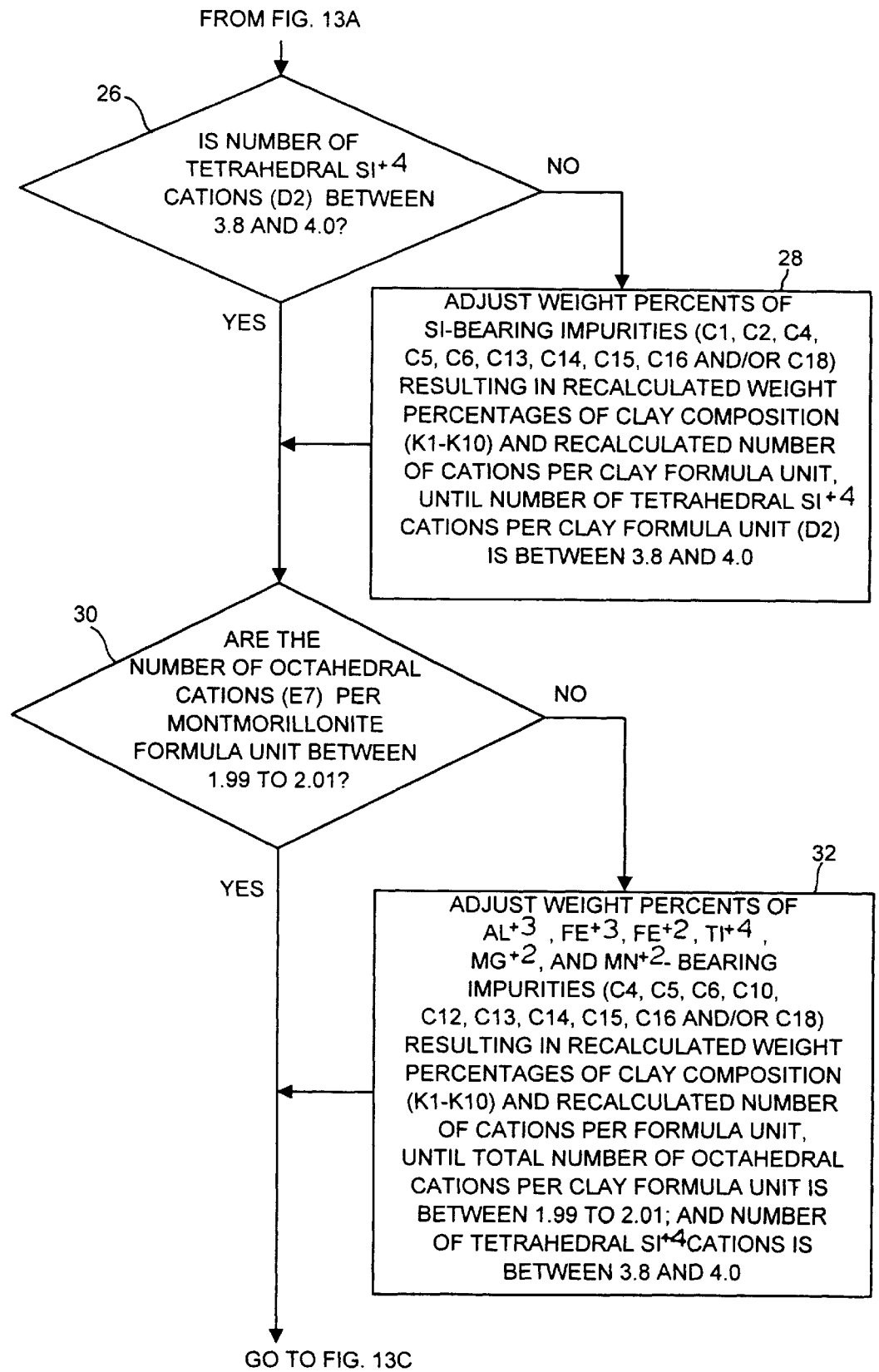
Figure 13C:
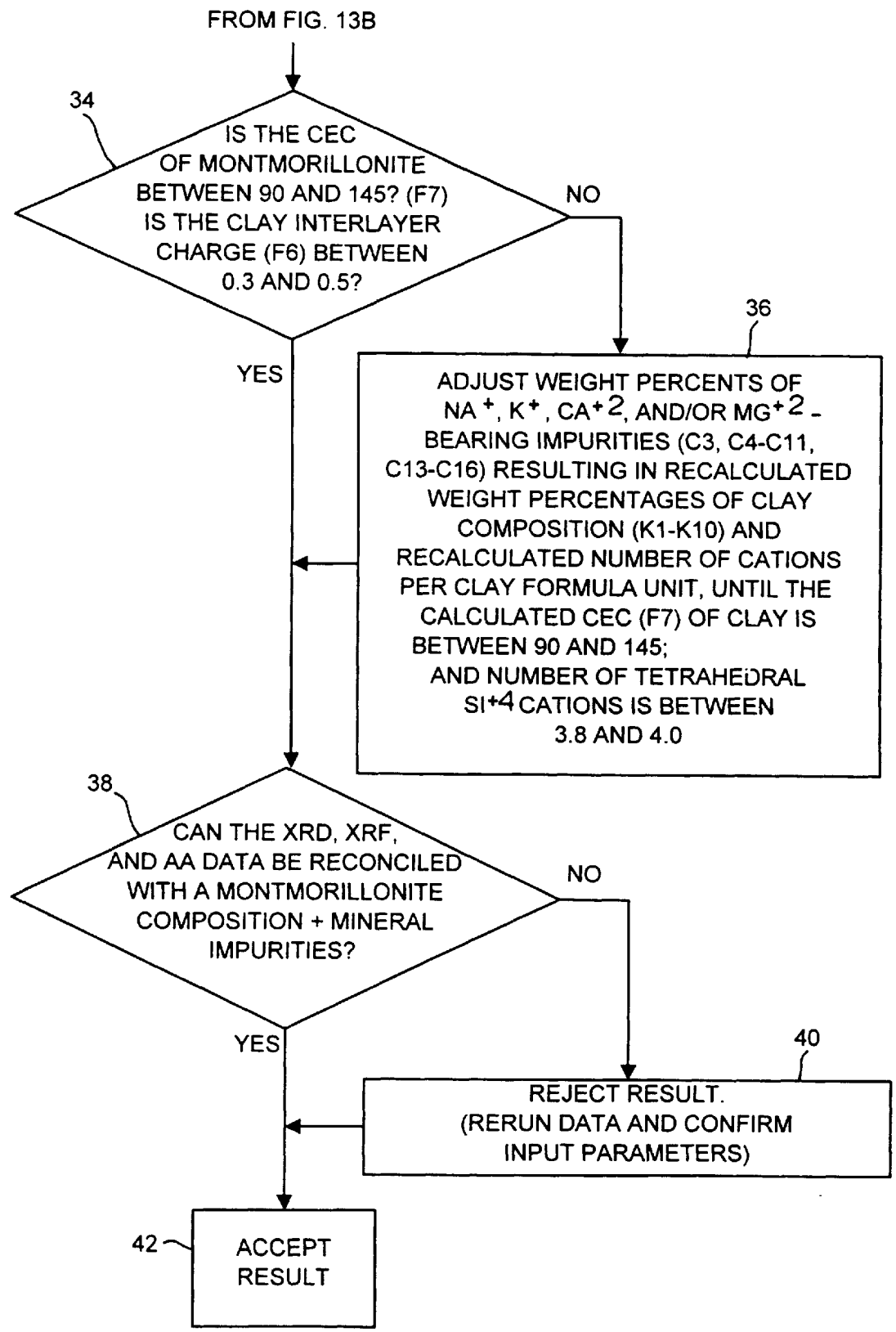

In one embodiment of the present invention, the above-described iterative determination of the components of a clay composition can be accomplished efficiently by computer program. FIGS. 13A–C is a flow chart of a computer calculation routine 10 for calculating and recalculating the composition of a clay deposit being analyzed. The flow chart of FIGS. 13A–C and the following description thereof, references various grids and cells shown in FIG. 1. The computer program calculation routine 10 is performed on a representative clay deposit sample for calculating a final clay composition, including impurities, as described with reference to Examples 1, 2 and 3 and shown in FIGS. 5, 8 and 12, respectively.

At step 12 of the computer program calculation routine 10 of FIGS. 13A–C, the elemental constituents of the sample are entered into Grid #1, cells A1–A13, e.g., from an x-ray fluorescence analysis of the clay composition. At step 14, the bulk chemical analysis (elemental analysis) is converted into weight percent of dioctahedral smectite clay, e.g., montmorillonite clay, component oxides in Grid #2, cells K1–K10, assuming that no non-montmorillonite components (impurities) are included in the clay composition. A determination is made at step 16 as to whether crystalline impurities of the sample have been quantified. If so, its crystalline impurities or mineral abundances then can be quantified in step 18. If not, the crystalline impurities or mineral abundances can be estimated in step 20. In the case of step 18, weight percentages are calculated from XRD impurity peak integration and are entered into Grid #7, cells C1–C19. In the case of step 20, the weight percentages of impurities can be estimated from the XRD pattern based on peak position and relative peak height in step 20, and entered in Grid #7, cells C1–C19.

From the crystalline mineral abundances (impurities) entered in step 18 or 20, the computer calculates a reduction in montmorillonite clay composition components (oxides) in Grid #1, cells K1–K10 in step 22 by reducing the weight percent of montmorillonite components (oxides) based on the weight percent of any impurity containing a montmorillonite component oxide; e.g., see FIG. 4, of Example 1; FIG. 8 of Example 2; and FIG. 11 of Example 3. This recalculated clay composition of step 22 then is converted into the number of metal cations per clay formula unit in step 24 to provide the number of each cation in each formula unit of the clay tetrahedral layer (Grid #3, cells D1–D3), clay octahedral layer (Grid #4, cells E1–E6) and clay interlayer (Grid #5, cells F1–F4). If the recalculated number of $Si^{+4}$ cations per clay formula unit in the tetrahedral clay layer (Grid #3, cell D2) is not between 3.8 and 4.0 (step 26), the weight percents of Si-bearing impurities (Grid #7, cells C1, C2, C4, C5, C6, C13, C14, C15, C16 and/or C18) are adjusted in step 28, usually by reducing the weight percents (usually due to an amorphous $SiO_2$-containing impurity) to arrive at 3.8 to 4.0 octahedral $Si^{+4}$ cations per formula unit, resulting in recalculated weight percentages of clay—composition (K1–K10) and recalculated numbers of cations per montmorillonite formula unit (F1–F3; E1–E6; and F1–F4), until the number of tetrahedral $Si^{+4}$ cations per clay formula unit (D2) is between 3.8 and 4.0.

The number of tetrahedral $Si^{+4}$ cations per montmorillonite formula unit calculated in step 26 is compared to the acceptable range of 3.8 to 4.0, and/or, after the weight percentages are recalculated at step 28, the sum of the number of octahedral cations per clay formula unit (E7) is compared to its acceptable range of 1.99 to 2.01 in step 30. If the total number of tetrahedral $Si^{+4}$ cations per montmorillonite formula unit is not in the range of 3.8 to 4.0, or if the total number of octahedral cations per clay formula unit (E7) is not between 1.99 and 2.01 in step 30, the weight percentages of $Si^{+4}$-bearing impurities is adjusted in step 28 and/or the weight percentages of $Al^{+3}$-, $Fe^{+3}$-, $Fe^{+2}$-, $Ti^{+4}$-, $Mg^{+2}$- and/or $Mn^{+2}$-bearing impurities is adjusted in step 32 (Grid #7, cells C4–C6, C10, C12–C16 and/or C18) resulting in recalculated weight percentages of clay composition components (Grid #2, cells K1–K10), and the number of cations per clay formula unit (D1–D4, E1–E7 and F1–F5) is recalculated until the total number of tetrahedral $Si^{+4}$ cations per clay formula unit is in the range 3.8 to 4.0, and the total number of octahedral cations per clay formula unit (E7) is between 1.99 and 2.01.

If the sum of the number of octahedral cations is between 1.99 and 2.01, as determined at step 30, or determined after the number of cations is recalculated at step 32, the CEC or cation exchange capacity (F7) and clay charge (F6) of the clay are compared to their corresponding acceptable ranges at step 34, based on the revised cation distribution in the interlayer (F1–F4). The cation exchange capacity or CEC (F7) should be between 90 and 145, usually between 90 and 140, and most often between 115 and 130. The interlayer charge (F6) should be between 0.3 and 0.5.

If the CEC is not between 90 and 145 and/or if the interlayer charge (F6) is not between 0.3 and 0.5 (step 34), the weight percentages of $Na^+$-, $K^+$-, $Ca^{+2}$- and/or $Mg^{+2}$-bearing impurities (C3, C4–C10, and/or C13–C16) are adjusted in step 36, resulting in recalculated weight percentages of clay composition components or oxides (K1–K10) and recalculated number of cations per clay formula unit (D1–D3; E1–E6; and/or F1–F4), until the calculated CEC (F7) is between 90 and 145; the interlayer clay charge (F6) is between 0.3 and 0.5; the number of tetrahedral $Si^{+4}$ cations per clay formula unit (D2) is between 3.8 and 4.0; and the total number of octahedral cations per clay formula unit (E7) is between 1.99 and 2.01. When all these conditions are met (clay charge (F6)=0.3–0.5; sum of octahedral cations per clay formula unit (E7)=1.99–2.01; number of tetrahedral $Si^{+4}$ cations per clay formula unit (D2)=3.8–4.0; and CEC (F7)=90–145) the clay composition is acceptably accurate and the amount and type of impurities have been substantially quantified, see Example 1, FIG. 5; Example 2, FIG. 8; and Example 3, FIG. 12. The amorphous impurities are calculated by quantifying the crystalline impurities by XRD and subtracting the quantity of crystalline impurities from the total quantity of impurities by the above analysis.

At step 38, the final clay composition should have a total number of tetrahedral $Si^{+4}$ cations per clay formula unit between 3.8 and 4.0; the interlayer charge should be between 0.3 and 0.5; the cation exchange capacity should be between 90 and 145 milliequivalents per 100 grams; and the sum of the octahedral cations per clay formula unit should be in the range of 1.99 to 2.01. If these criteria are not met, in step 38, then the results are rejected in step 40 and the computer clay composition calculation routine 10 is started over, checking the input data. If these criteria are met, the clay composition results are accepted at step 42.

The actual measurement of cation exchange capacity or CEC of the clay sample (calculated at Grid #6, cell F7 and at step 34 of the computer calculation routine flow diagram of FIGS. 13A–C), as well as the actual number of $Mg^{+2}$ interlayer cations per formula units (Grid #6, cell G1), such as by atomic absorption or AA can be performed on each clay sample as a check against the above-described iterative analysis, but usually are not necessary, or may be performed on the first clay sample from a particular deposit and thereafter need not be part of the analysis. Similarly, an actual analysis of the $Fe^{+2}/Fe^{+3}$ ratio or $Fe^{+2}$/total $Fe^{+2}$ and $Fe^{+3}$ cations (Grid #1A, cell B1) is a good check for assignment of $Fe^{+3}$ cations to either the tetrahedral layer (Grid #3, cell D3) or to the octahedral layer (Grid #4, cell E2), but are not necessary to the process of the present invention. The anions (Grid #8) always total 11 per formula unit, for montmorillonite clay samples, to balance the cations per formula unit.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A method of determining a quantity of amorphous $SiO_2$-containing impurities in a montmorillonite clay sample comprising the steps of:

(a) analyzing the clay sample to determine the weight percent of $SiO_2$ contained in the clay sample based on a formula for montmorillonite clay and calculated from an elemental analysis of the clay sample, assuming that the clay sample is 100% montmorillonite clay;

(b) analyzing the clay sample to determine the weight percent of non-montmorillonite $SiO_2$-containing crystalline impurities;

(c) calculating the weight percent of $SiO_2$ from step (a) that is derived from the montmorillonite clay portion of the sample and the amorphous $SiO_2$-containing impurities by subtracting the weight percent of $SiO_2$-containing crystalline impurities in step (b) from the weight percent of $SiO_2$ in step (a);

(d) comparing the calculated weight percent of $SiO_2$ found in step (c) with one or more properties of the clay sample;

(e) reducing the weight percent of $SiO_2$ found in step (c) until the reduced weight percent of $SiO_2$ is consistent with one or more properties of the clay sample—the reduced weight percent of $SiO_2$ approximating the weight percent of montmorillonite-derived $SiO_2$; and (f) subtracting the weight percent of montmorillonite-derived $SiO_2$ found in step (e) from the weight percent $SiO_2$ found in step (c) to determine the approximate weight percent of amorphous $SiO_2$-containing impurities in the clay sample.

2. The method of claim 1, wherein the amount of further lowering of the quantity of $SiO_2$ determined in step (d) is determined by reducing the montmorillonite-derived $SiO_2$ calculated in step (c) until the number of montmorillonite-derived $Si^{+4}$ cations is in the range of 3.8 to 4.0.

3. The method of claim 1, wherein the amount of further lowering of the quantity of $SiO_2$ determined in step (d) is determined by reducing the montmorillonite-derived $SiO_2$ calculation in step (c) until the number of octahedral cations is about 2.0.

4. The method of claim 1, wherein the amount of further lowering of the quantity of $SiO_2$ determined in step (d) is determined by reducing the montmorillonite-derived $SiO_2$ calculated in step (c) until the interlayer charge, in number of interlayer cations per montmorillonite clay formula unit, is in the range of 0.3 to 0.5.

5. The method of claim 1, wherein the amount of further lowering of the quantity of $SiO_2$ determined in step (d) is determined by reducing the montmorillonite-derived $SiO_2$ calculated in step (c) until the interlayer charge, in number of interlayer cations per montmorillonite clay formula unit, is in the range of 0.35 to 0.45.

6. The method of claim 1, wherein the amount of further lowering of the quantity of $SiO_2$ determined in step (d) is determined by reducing the montmorillonite-derived $SiO_2$ calculated in step (c) until the cation exchange capacity of the montmorillonite clay is in the range of 90 to 145 milliequivalents per 100 grams of the montmorillonite clay.

7. The method of claim 1, wherein the amount of further lowering of the quantity of $SiO_2$ determined in step (d) is determined by reducing the montmorillonite-derived $SiO_2$ calculated in step (c) until the cation exchange capacity of the montmorillonite clay is in the range of 90 to 145 milliequivalents per 100 grams of the montmorillonite clay.

8. The method of claim 1, wherein the amount of further lowering of the quantity of $SiO_2$ determined in step (d) is determined by reducing the montmorillonite-derived $SiO_2$ calculated in step (c) until the cation exchange capacity of the montmorillonite clay is in the range of 115 to 130 milliequivalents per 100 grams of the montmorillonite clay.

9. The method of claim 1, wherein at least a portion of the crystalline non-montmorillonite $SiO_2$-containing impurities in step (b) are found by x-ray diffraction.

10. The method of claim 9, wherein the interlayer charge is determined, at least in part, by calculating an amount of a montmorillonite-derived oxide selected from the group consisting of $Na_2O$, $CaO$, $MgO$, $K_2O$, and mixtures, assuming that there are no impurities containing Na, Ca, Mg or K, and then reducing the amount of the montmorillonite-derived oxide selected from the group consisting of $Na_2O$, $CaO$, $MgO$, $K_2O$, and mixtures, until the sum of the number of $Na^+$, $Ca^{+2}$, $Mg^{+2}$ and $K^+$ cations per montmorillonite clay formula unit is in the range of 0.3 to 0.5.

11. The method of claim 10, further including the step of reducing the amount of montmorillonite-derived oxide selected from the group consisting of $Na_2O$, $CaO$, $MgO$, $K_2O$ and mixtures, until the cation exchange capacity of the montmorillonite clay is in the range of 90 to 145 milliequivalents of charge per montmorillonite formula unit.

12. The method of claim 10, further including the step of reducing the amount of montmorillonite-derived oxide selected from the group consisting of $Na_2O$, $CaO$, $MgO$, $K_2O$ and mixtures, until the cation exchange capacity of the montmorillonite clay is in the range of 90 to 140 milliequivalents of charge per montmorillonite formula unit.

13. The method of claim 11, further including the step of reducing the amount of montmorillonite-derived oxide selected from the group consisting of $Na_2O$, $CaO$, $MgO$, $K_2O$ and mixtures, until the cation exchange capacity of the montmorillonite clay is in the range of 115 to 130 milliequivalents of charge per montmorillonite formula unit.

14. The method of claim 11, further including the step of calculating the cation exchange capacity by reducing the number of $Al^{+3}$ cations per formula unit in a clay layer selected from the group consisting of tetrahedral layer, an octahedral, and a combination of the tetrahedral layer and the octahedral layer, based on the $Al^{+3}$-containing contaminants found in the montmorillonite clay sample.

15. The method of claim 14, wherein the $Al^{+3}$-contaminants found in the montmorillonite clay sample is determined by reducing an amount of montmorillonite-derived $SiO_2$ and $Al_2O_3$ until the number of $Si^{+4}$ and $Al^{+3}$ cations per montmorillonite clay formula unit assigned to the tetrahedral layer is 4.0, the amount of reduction in weight percent of montmorillonite-derived $SiO_2$ and $Al_2O_3$.

16. A method of determining a quantity of amorphous $SiO_2$-containing impurities in a montmorillonite clay sample comprising the steps, performed by a data processing system, of:

(a) analyzing the clay sample to determine the weight percent of $SiO_2$ contained in the clay sample based on a formula for montmorillonite clay and calculated from an elemental analysis of the clay sample, assuming that the clay sample is 100% montmorillonite clay;

(b) analyzing the clay sample to determine the weight percent of non-montmorillonite $SiO_2$-containing crystalline impurities;

(c) calculating the weight percent of $SiO_2$ from step (a) that is derived from the montmorillonite clay portion of the sample and the amorphous $SiO_2$-containing impurities by subtracting the weight percent of $SiO_2$-containing crystalline impurities in step (b) from the weight percent of $SiO_2$ in step (a);

(d) comparing the calculated weight percent of $SiO_2$ found in step (c) with one or more properties of the clay sample; and (e) reducing the weight percent of $SiO_2$ found in step (c) until the reduced weight percent of $SiO_2$ is consistent with one or more properties of the clay sample—the reduced weight percent of $SiO_2$ being proportional to the weight percent of montmorillonite-derived $SiO_2$.

17. The method of claim 16, wherein the amount of further lowering of the quantity of $SiO_2$ determined in step (d) is determined by reducing the montmorillonite-derived $SiO_2$ calculated in step (c) until the number of montmorillonite-derived $Si^{+4}$ cations is in the range of 3.8 to 4.0.

18. The method of claim 16, wherein the amount of further lowering of the quantity of $SiO_2$ determined in step (d) is determined by reducing the montmorillonite-derived $SiO_2$ calculation in step (c) until the number of octahedral cations is about 2.0.

19. The method of claim 16, wherein the amount of further lowering of the quantity of $SiO_2$ determined in step (d) is determined by reducing the montmorillonite-derived $SiO_2$ calculated in step (c) until the interlayer charge, in number of interlayer cations per montmorillonite clay formula unit, is in the range of 0.3 to 0.5.

20. The method of claim 16, wherein the amount of further lowering of the quantity of $SiO_2$ determined in step (d) is determined by reducing the montmorillonite-derived $SiO_2$ calculated in step (c) until the interlayer charge, in number of interlayer cations per montmorillonite clay formula unit, is in the range of 0.35 to 0.45.

21. The method of claim 16, wherein the amount of further lowering of the quantity of $SiO_2$ determined in step (d) is determined by reducing the montmorillonite-derived $SiO_2$ calculated in step (c) until the cation exchange capacity of the montmorillonite clay is in the range of 90 to 145 milliequivalents per 100 grams of the montmorillonite clay.

22. The method of claim 16, wherein the amount of further lowering of the quantity of $SiO_2$ determined in step (d) is determined by reducing the montmorillonite-derived $SiO_2$ calculated in step (c) until the cation exchange capacity of the montmorillonite clay is in the range of 90 to 145 milliequivalents per 100 grams of the montmorillonite clay.

23. The method of claim 16, wherein the amount of further lowering of the quantity of $SiO_2$ determined in step (d) is determined by reducing the montmorillonite-derived $SiO_2$ calculated in step (c) until the cation exchange capacity of the montmorillonite clay is in the range of 115 to 130 milliequivalents per 100 grams of the montmorillonite clay.

24. The method of claim 16, wherein at least a portion of the crystalline non-montmorillonite $SiO_2$-containing impurities in step (b) are found by x-ray diffraction.

25. The method of claim 24, wherein the interlayer charge is determined, at least in part, by calculating an amount of a montmorillonite-derived oxide selected from the group consisting of $Na_2O$, $CaO$, $MgO$, $K_2O$, and mixtures, assuming that there are no impurities containing Na, Ca, Mg or K, and then reducing the amount of the montmorillonite-derived oxide selected from the group consisting of $Na_2O$, $CaO$, $MgO$, $K_2O$, and mixtures, until the sum of the number of $Na^+$, $Ca^{+2}$, $Mg^{+2}$ and $K^+$ cations per montmorillonite clay formula unit is in the range of 0.3 to 0.5.

26. The method of claim 25, further including the step of reducing the amount of montmorillonite-derived oxide selected from the group consisting of $Na_2O$, $CaO$, $MgO$, $K_2O$ and mixtures, until the cation exchange capacity of the montmorillonite clay is in the range of 90 to 145 milliequivalents of charge per montmorillonite formula unit.

27. The method of claim 25, further including the step of reducing the amount of montmorillonite-derived oxide selected from the group consisting of $Na_2O$, $CaO$, $MgO$, $K_2O$ and mixtures, until the cation exchange capacity of the montmorillonite clay is in the range of 90 to 145 milliequivalents of charge per 100 grams of montmorillonite clay.

28. The method of claim 26, further including the step of reducing the amount of montmorillonite-derived oxide selected from the group consisting of $Na_2O$, $CaO$, $MgO$, $K_2O$ and mixtures, until the cation exchange capacity of the montmorillonite clay is in the range of 115 to 130 milliequivalents of charge per 100 grams of montmorillonite clay.

29. The method of claim 26, further including the step of calculating the cation exchange capacity by reducing the number of $Al^{+3}$ cations per formula unit in a clay layer selected from the group consisting of tetrahedral layer, an octahedral, and a combination of the tetrahedral layer and the octahedral layer, based on the $Al^{+3}$-containing contaminants found in the montmorillonite clay sample.

30. The method of claim 29, wherein the $Al^{+3}$-contaminants found in the montmorillonite clay sample is determined by-:educing an amount of montmorillonite-derived $SiO_2$ and $Al_2O_3$ until the number of $Si^{+4}$ and $Al^{+3}$ cations per montmorillonite clay formula unit assigned to the tetrahedral layer is 4.0, the amount of reduction in weight percent of montmorillonite-derived $SiO_2$ and $Al_2O_3$.

* * * * *